(12) United States Patent
Ellis et al.

(10) Patent No.: US 11,950,998 B2
(45) Date of Patent: Apr. 9, 2024

(54) INTRAOCULAR LENS INSERTION DEVICE

(71) Applicant: JelliSee Ophthalmics Inc., McLean, VA (US)

(72) Inventors: Forrest J. Ellis, McLean, VA (US); Nestor O. Farmiga, Rochester, NY (US)

(73) Assignee: JelliSee Ophthalmics Inc., McLean, VA (US)

( * ) Notice: Subject to any disclaimer, the term of this patent is extended or adjusted under 35 U.S.C. 154(b) by 0 days.

(21) Appl. No.: 18/295,912

(22) Filed: Apr. 5, 2023

(65) Prior Publication Data
US 2023/0310144 A1    Oct. 5, 2023

Related U.S. Application Data

(60) Provisional application No. 63/327,480, filed on Apr. 5, 2022.

(51) Int. Cl.
*A61F 2/16* (2006.01)

(52) U.S. Cl.
CPC ............ *A61F 2/1613* (2013.01); *A61F 2/167* (2013.01); *A61F 2/1678* (2013.01); *A61F 2002/1681* (2013.01)

(58) Field of Classification Search
CPC ....................................................... A61F 2/167
See application file for complete search history.

(56) References Cited

U.S. PATENT DOCUMENTS

| | | | | |
|---|---|---|---|---|
| 6,976,989 | B1 * | 12/2005 | Vincent | A61F 2/167 606/107 |
| 2004/0117012 | A1 * | 6/2004 | Vincent | A61F 2/167 606/107 |
| 2011/0144653 | A1 * | 6/2011 | Pankin | A61F 2/1678 606/107 |
| 2020/0405475 | A1 * | 12/2020 | Zacher | A61F 2/167 |

FOREIGN PATENT DOCUMENTS

WO    WO-2020032023 A1 *    2/2020    ............. A61F 2/167

* cited by examiner

*Primary Examiner* — Javier G Blanco
(74) *Attorney, Agent, or Firm* — TAROLLI, SUNDHEIM, COVELL & TUMMINO L.L.P.

(57) ABSTRACT

An insertion system for inserting an IOL int a patient's eye is provided. The insertion system includes a pusher and an introducer sheath with a back housing and a front housing. The front housing includes a longitudinally extending IOL rolling member with a proximal section, an intermediate section, a distal section and a longitudinally extending lumen defined by an upper face and a lower face. The lower face has opposing inner peripheral edges. The radius of curvature of the upper face and the lower face decreases from the proximal section to the distal section and the distance between the opposing inner peripheral edges decreases from the proximal section to the distal section.

10 Claims, 37 Drawing Sheets

Cross- Section A-A

Cross- Section B-B

INTRAOCULAR LENS INSERTION DEVICE

CROSS-REFERENCE TO RELATED APPLICATIONS

The current application claims priority to U.S. Provisional Application No. 63/327,480 filed on Apr. 5, 2022 and incorporated by reference in its entirety.

TECHNICAL FIELD

The present disclosure relates to an insertion system to insert an intraocular lens into a patient's eye.

BACKGROUND

Cataract surgery is one of the most common surgical procedure performed each year throughout the world. Approximately 3 million cataract surgeries are performed each year in the United States of America. A cataract is a gradual clouding of the natural lens of the human eye. This clouding results in blurred vision that is correctable with surgical removal of the cataract and, in most cases, placement of a clear artificial intraocular lens (IOL). Modern IOLs include an optic or lens body for focusing light on the retina of the eye. In addition, IOLs include one or more arms (e.g. haptics) that extend outward from the optic body and that facilitate centering the IOL in the desired location within the eye (typically within the lens capsular bag).

Modern cataract removal surgery is performed through a small incision in the periphery of the cornea. Modern IOLs are designed to be deformed such as rolled or folded to a relatively small profile, and then allowed to return to their original shape within the eye. This reduces trauma and facilitates post-operative healing.

Various inserters are available to both fold an IOL and allow insertion of the IOL into the eye in a controlled manner. Inserters for delivering IOLs into the eye typically employ a handpiece and a cartridge having a hollow insertion tube or cannula through which the folded IOL is passed using a pusher. The cartridges are often fabricated from disposable materials, such as plastics, and remain in a sterile package until ready for coupling with the handpiece. Conventional IOL cartridges include a loading chamber connected to the insertion tube. In many popular versions, the loading chamber is formed by two hinged halves which receive the IOL and which close to fold the IOL. A non-folding cartridge can also be used in which instruments (e.g. forceps) are used to insert the IOL into a proximal or rear opening of the cartridge. The injection tube includes a small diameter distal end that is insertable into the incision within the eye. After mating the cartridge with the handpiece (if a separate cartridge is used), the pusher urges the IOL through the loading chamber and through the insertion tube into the eye. The distal end of the cartridge is beveled into a sharp point that enables insertion through the corneal incision and facilitates controlled expulsion and manipulation of the IOL into the capsular bag. However, sometimes the IOL is damaged during the process of forcing the IOL through the insertion tube. Sometimes, the IOL rolls or folds improperly such that it does not unfold (unroll) in a controlled and desired manner during placement of the IOL into the eye (into the lens capsular bag). Some inserters do without the cartridge and may be reusable.

Current inserters do not have internal elements that simultaneously roll or fold the optic and haptics as the IOL passes along the insertion tube. As such, an inserter that properly and reliably rolls or folds the IOL optic and the haptics is needed to facilitate reliable placement of the IOL in the capsular bag of the eye.

SUMMARY

An insertion system for inserting an IOL into a patient's eye is provided. In an aspect, an insertion system comprises a pusher having a longitudinally extending axis and a proximal portion and a distal portion. The proximal portion can include an actuator and the distal portion can comprise a deformable and longitudinally extending first prong and a deformable and longitudinally extending second prong. The insertion system can also include an introducer sheath comprising a back housing, a front housing, and a distal end. The back housing can define a first longitudinally extending lumen sized and configured to slidably receive the first prong of the pusher and a second longitudinally extending lumen sized and configured to slidably receive the second prong of the pusher. A chamber can be located at a distal portion of the back housing and can have a distal opening and a proximal abutment face configured to contact the pusher in a fully deployed position to limit the amount that the proximal portion of the pusher may extend to or beyond a distal portion of the introducer sheath. The front housing can include a receptacle located at a proximal portion thereof that is sized and configured to receive the IOL and fit within the chamber of the back housing in an assembled configuration. The front housing also includes a longitudinally extending IOL rolling member in fluid communication with the receptacle. The IOL rolling member has a proximal section, an intermediate section, a distal section and a longitudinally extending lumen defined by an upper face and a lower face. The lower face has opposing inner peripheral edges. The radius of curvature of the upper face and the lower face decreases from the proximal section to the distal section and the distance between the opposing inner peripheral edges decreases from the proximal section to the distal section. The distal end is in fluid communication with the distal section of the IOL rolling member.

In an aspect a kit is provided that includes an insertion system and an IOL. The IOL has an anterior face located anterior to the equator and a posterior face located posterior to the equator. Each of the anterior face and the posterior face has an anterior surface, a posterior surface, and a periphery. A side wall extends across the equator and extends from the anterior face to the posterior face. A chamber is located between the anterior face and the posterior face and contains a material. At least two opposing haptics are connected to the periphery of the anterior face, the posterior face or both.

DETAILED DESCRIPTION

Figure 1:
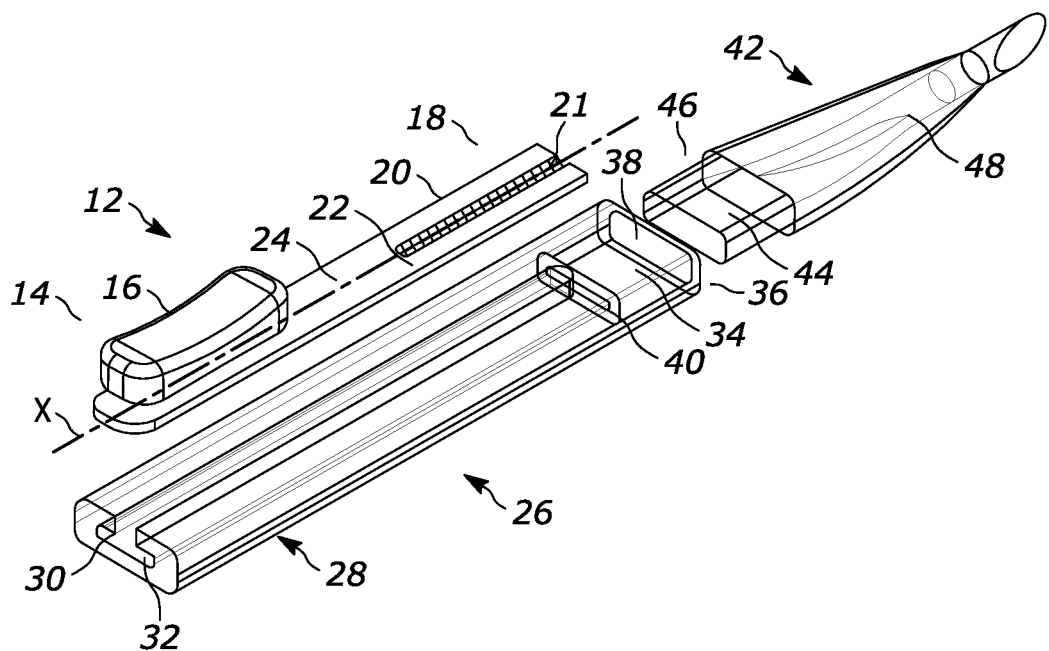
FIG. 1 is a perspective view of unassembled components of an insertion system include a pusher and an introducer sheath according to an aspect of the present disclosure.

The present disclosure relates to an IOL insertion system to insert an IOL, including an accommodative IOL, into a patient's eye. As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. The terms "first," "second," etc. are used to distinguish one element from another and not used in a quantitative sense unless indicated otherwise. Thus, a "first" element described below could also be termed a "second" element. The terms "proximal" and "back" refer to a location, position or direction closer to the operator/clinician and the terms "distal" and "front" refer to a location, position, or direction closer to the patient. The terms "top" and "bottom" refer to the position of elements as depicted in the drawings. Similarly, the terms "upper" and "lower" refer to the position of elements as depicted in the drawings. As used herein a "patient" includes a mammal such as a human being. All IOL insertion systems as described herein are used for medical purposes and are therefore sterile.

Figure 2:
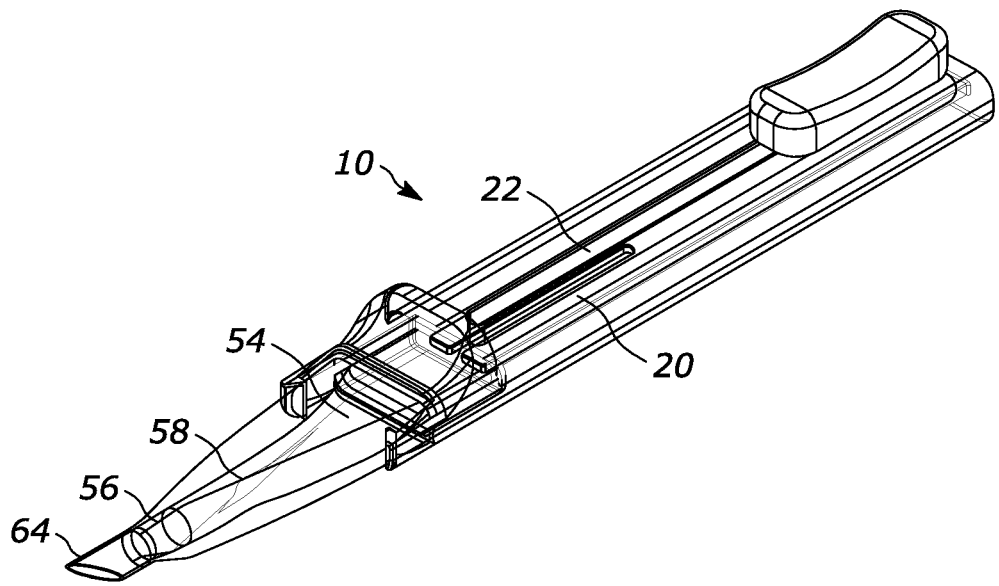
FIG. 2 is a perspective view of the insertion system of FIG. 1 depicting the pusher positioned in the back housing of the introducer sheath of FIG. 1.
Figure 3:
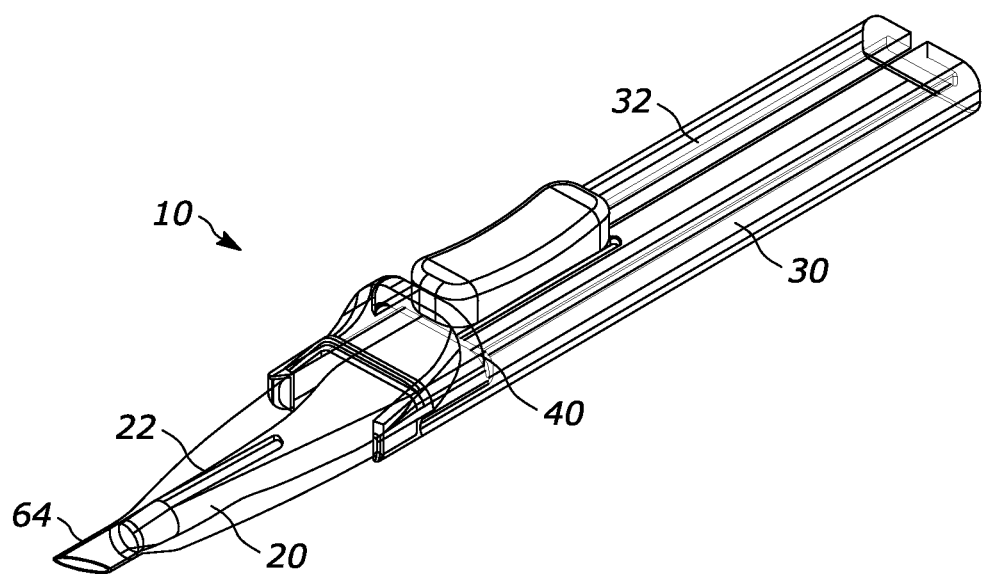
FIG. 3 is a perspective view of the insertion system of FIG. 1 depicting the distal prongs of the pusher positioned in the front housing of the introducer sheath.
Figure 6:
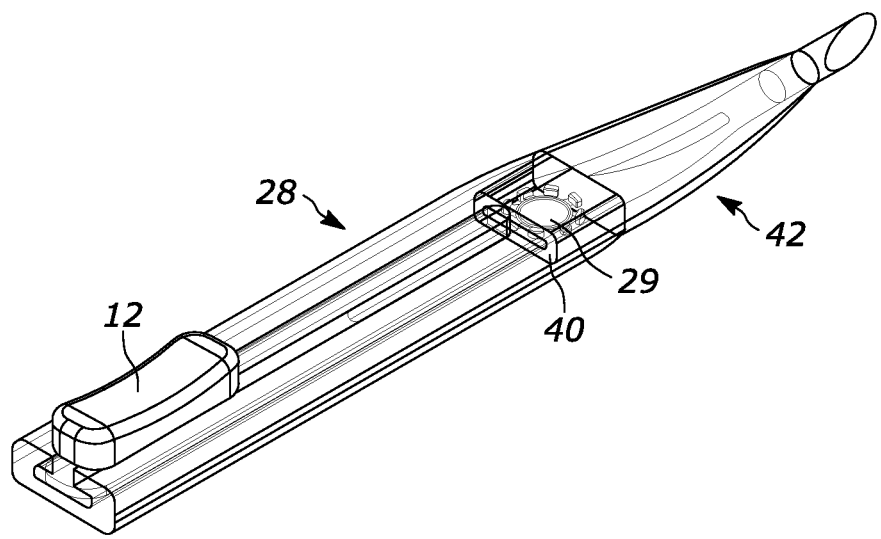
FIG. 6 is a perspective view of the introducer sheath of FIG. 5 in an assembled configuration with the pusher positioned in the back housing and contacting the IOL.
Figure 7B:
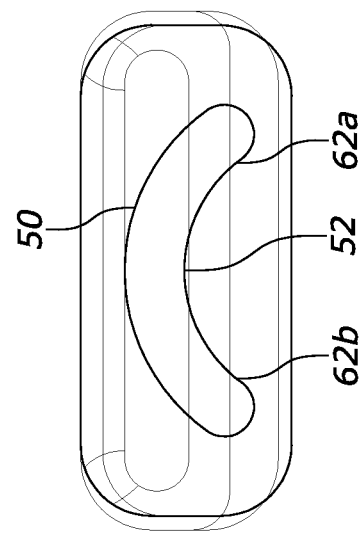
FIG. 7B is an end view of the section illustrated in FIG. 7A.
Figure 7A:
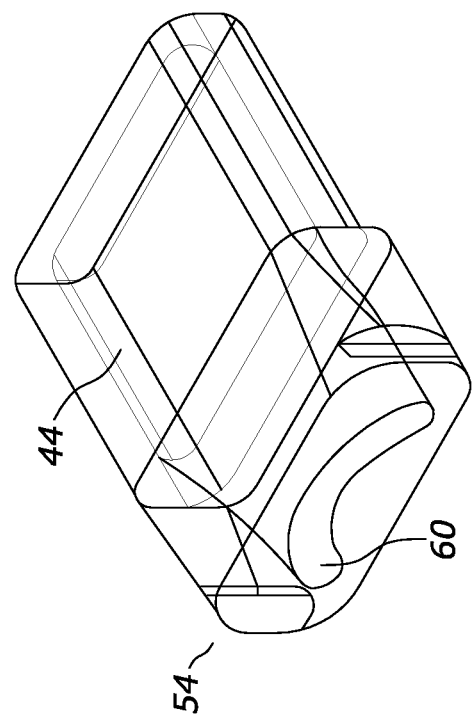
FIG. 7A is a cut-away view of a section of front housing of an introducer sheath illustrating the IOL rolling member including the lumen of the IOL rolling member according to an aspect of the present disclosure.
Figure 8B:
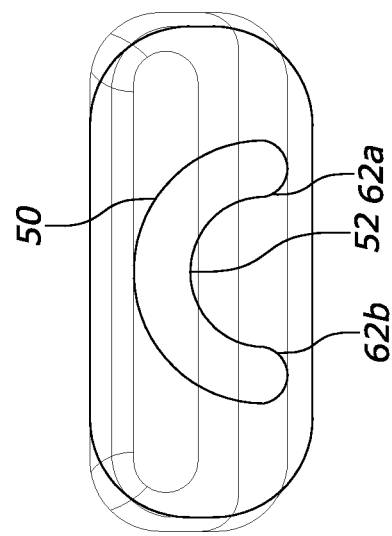
FIG. 8B is an end view of the section illustrated in FIG. 8A.
Figure 8A:
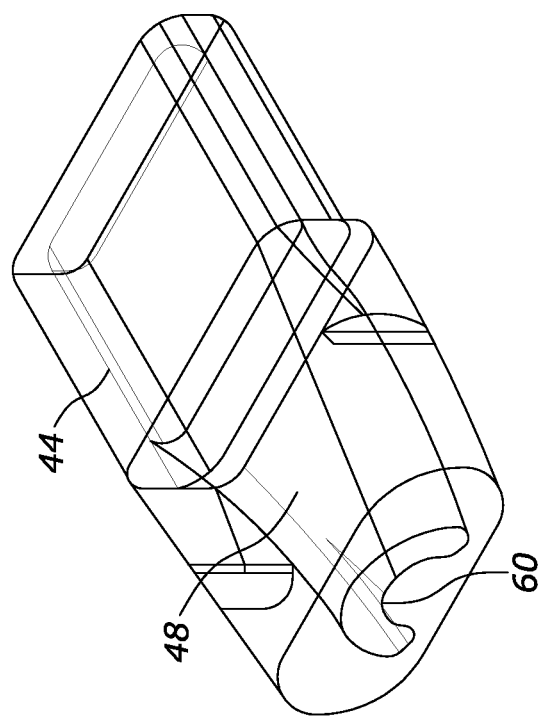
FIG. 8A is a cut-away view of a section of front housing of an introducer sheath illustrating the IOL rolling member including the lumen of the IOL rolling member according to an aspect of the present disclosure.
Figure 9B:
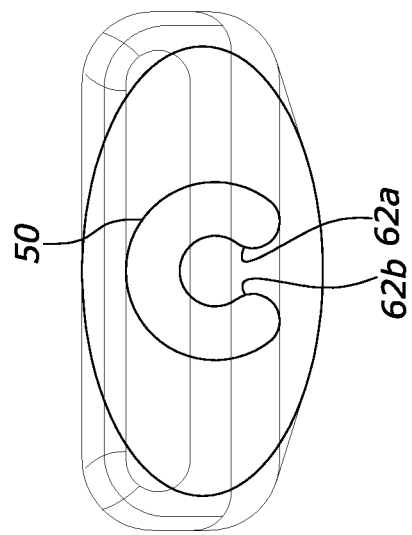
FIG. 9B is an end view of the section illustrated in FIG. 9A.
Figure 9A:
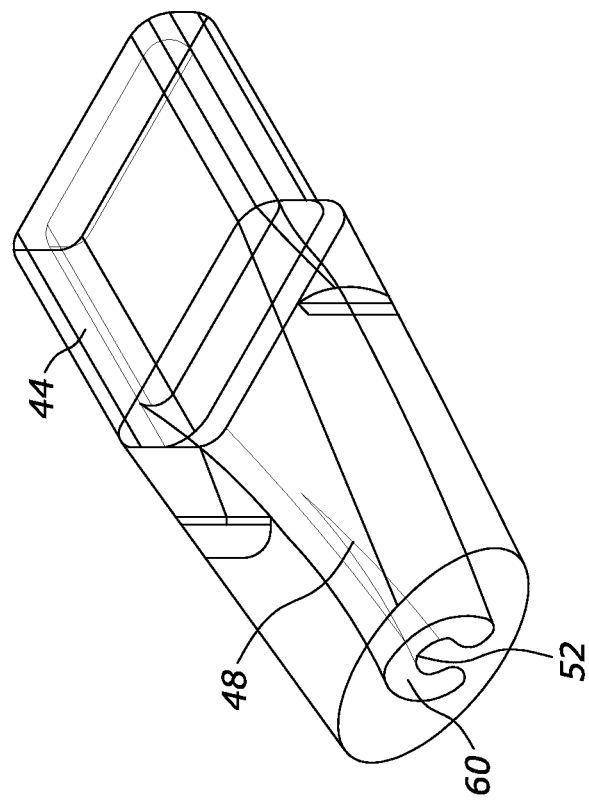
FIG. 9A is a cut-away view of a section of front housing of an introducer sheath illustrating the IOL rolling member including the lumen of the IOL rolling member according to an aspect of the present disclosure.
Figure 10B:
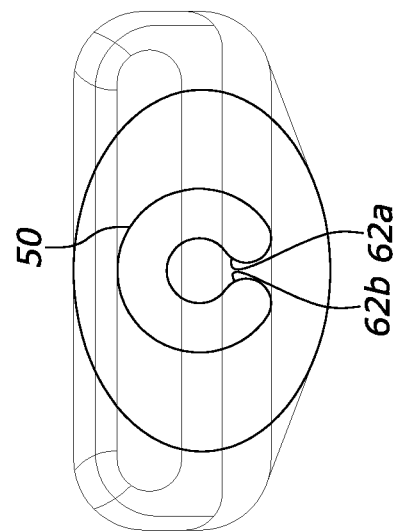
FIG. 10B is an end view of the section illustrated in FIG. 10A.
Figure 10A:
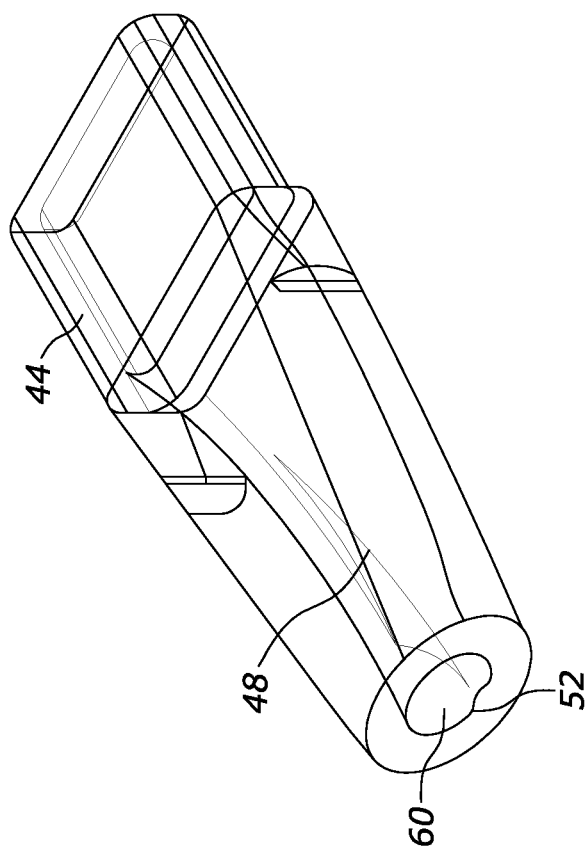
FIG. 10A is a cut-away view of a section of front housing of an introducer sheath illustrating the IOL rolling member including the lumen of the IOL rolling member according to an aspect of the present disclosure.
Figure 11B:
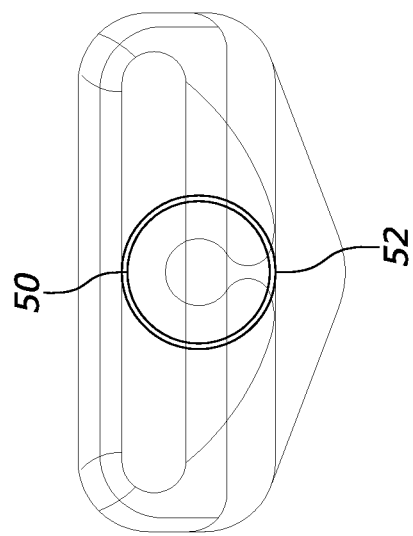
FIG. 11B is an end view of the section illustrated in FIG. 11A.
Figure 11A:
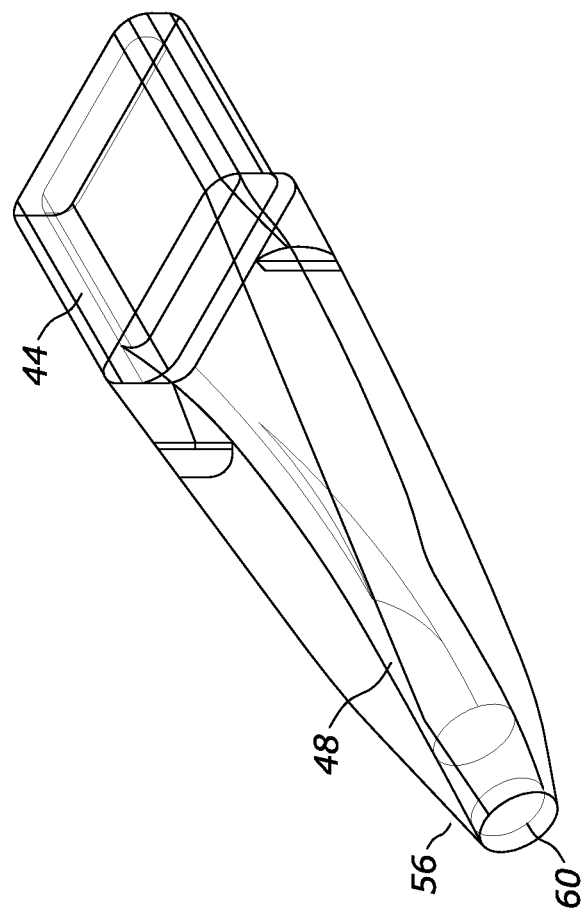
FIG. 11A is a cut-away view of a section of front housing of an introducer sheath illustrating the IOL rolling member including the lumen of the IOL rolling member according to an aspect of the present disclosure.

With reference to FIGS. 1-3, an insertion system 10 to insert an IOL into a patient's eye is provided. Insertion system can include pusher 12 and introducer sheath 26. Pusher 12 has a longitudinally extending axis X and can comprise proximal portion 14 and distal portion 18. In certain aspects, the pusher includes an intermediate portion 24 between the proximal portion and the distal portion. Proximal portion 14 can include actuator 16, which a user can press, for example, to urge the pusher through the introducer sheath as described in more detail below. Distal portion 18 can comprise deformable and longitudinally extending first prong 20 and deformable and longitudinally extending second prong 22. The first and second prongs can be unitary/connected with a membrane 21 (or similar structure) therebetween, for example, or can be separate and distinct prongs. Introducer sheath 26 of insertion system 10 can comprise back housing 28 and front housing 42. Back housing 28 can define first longitudinally extending lumen 30 sized and configured to slidably receive first prong 20 of pusher 12 and second longitudinally extending lumen 32 sized and configured to slidably receive second prong 22 of pusher 12. The longitudinally extending lumens need not extend through the entire length of the back housing. As depicted in FIGS. 1-3, the first longitudinally extending lumen and the second longitudinally extending lumen can be located on opposing sides of the back housing. FIG. 2 illustrates first prong 20 positioned in first lumen 30 and second prong 22 positioned in second lumen 32. Back housing 28 can include chamber 34 located at distal portion 36 of back housing 28. Chamber 34 can have distal opening 38 to allow an IOL 29 to pass through back housing 28 into front housing 42 as illustrated in FIG. 6. Chamber 34 can also have proximal abutment face 40 configured to contact pusher 12 in a fully deployed position as depicted in FIG. 3 to limit the amount proximal portion 14 of pusher 12 may extend to or beyond a distal portion of introducer sheath 26.

Figure 5:
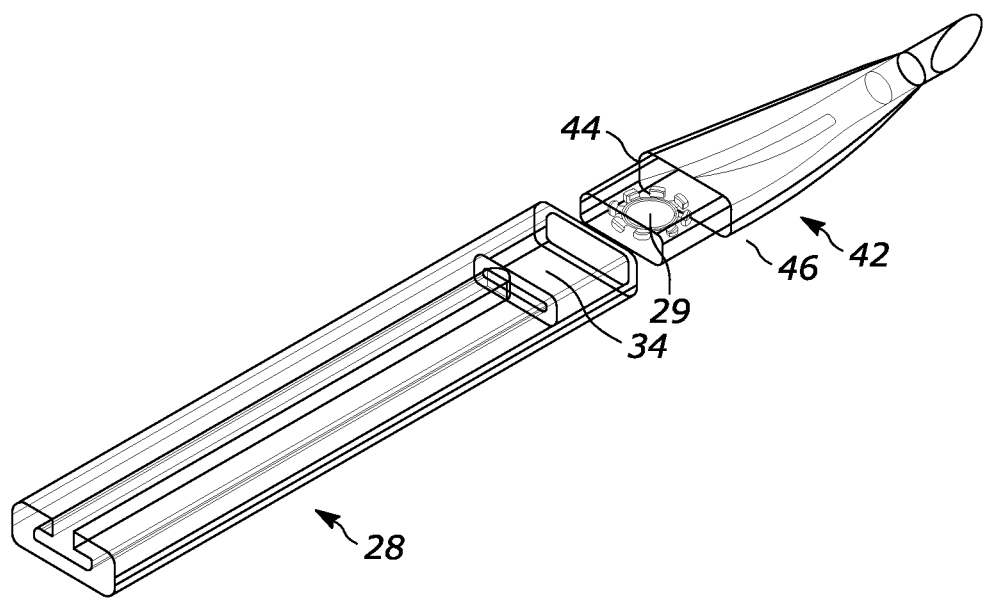
FIG. 5 is a perspective view of the front housing and the back housing of the introducer sheath of FIG. 1 in an unassembled configuration with an exemplary IOL positioned in the receptacle of the front housing.

Front housing 42 can comprises receptacle 44 located at proximal portion 46 of front housing 42 that is sized and configured to received IOL 29 as depicted in FIG. 5 and to fit within chamber 34 of back housing 28 in an assembled configuration as depicted in FIG. 6. Front housing 42 can further include longitudinally extending IOL rolling member 48, described in more detail below, having proximal section 54, intermediate section 58, distal section 56, and longitudinally extending lumen 60. Introducer sheath 26 can also include distal end 64 in fluid communication with distal section 56 of IOL rolling member 48.

Figure 4:
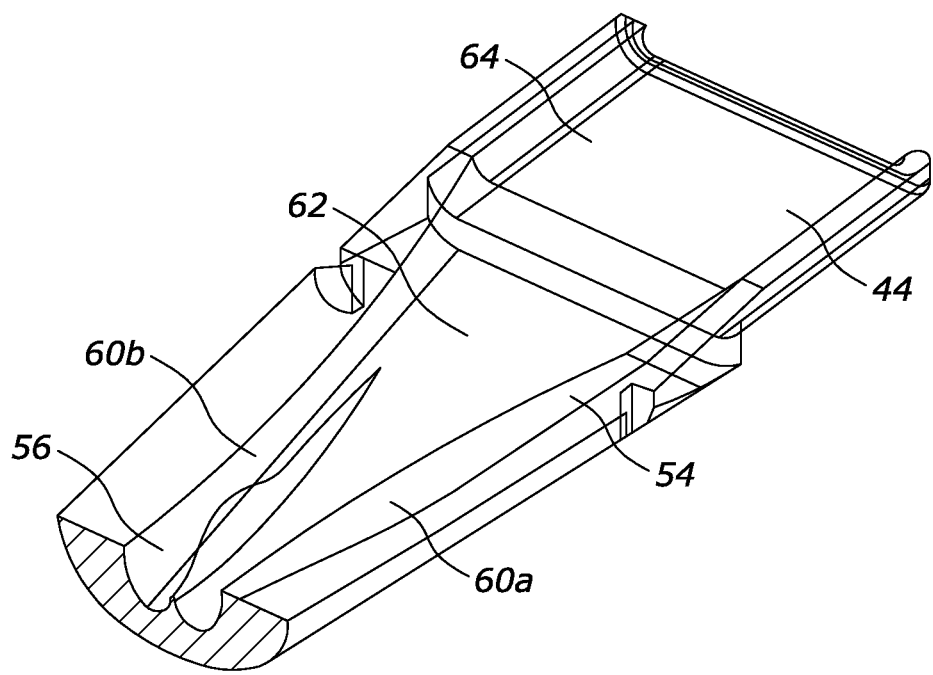
FIG. 4 is a partial view of the bottom surface of the front housing of FIG. 1 depicting the IOL rolling member according to an aspect of the present disclosure.

Regarding IOL rolling member 48, bottom surface 62 of lumen 60 of rolling member 48 is depicted in FIG. 4 as well as bottom surface 65 of receptacle 44. As also shown in FIG. 4, longitudinally extending lumen 60 of IOL rolling member 48 at proximal section 54 and intermediate section 56 can comprise a first side 60a sized and configured to slidably receive the first prong of the pusher and an opposing second side 60b sized and configured to slidably receive the second prong of the pusher. The first side and the second side of the IOL rolling member defining the lumen at the distal section thereof can be fluid communication with a single lumen defined by the distal end.

FIGS. 7-11 depict progressive partial cut-away views and corresponding end views of rolling member 48 from proximal section 54 to distal section 56. Lumen 60 can be defined by upper face 50 and lower face 52. Lower face 52 can comprise opposing inner peripheral edges 62a and 62b. As shown in FIGS. 7-11, the radius of curvature of upper face 50 and lower face 52 decreases from proximal section 54 to distal section 56 and the distance between opposing inner peripheral edges 62a and 62b decreases from proximal section 54 to distal section 56.

By having an IOL rolling member, the IOL can be rolled into the desired configuration and proper orientations. For example, any IOL has an anterior surface and a posterior surface. Some IOLs are designed to be inserted with the anterior surface as the "outside" of the rolled up IOL with the haptics rolled up within or extending below the IOL optic. As such, when the IOL unrolls into the lens capsule the haptics enter into the lens capsule first followed by the IOL optic. Some IOLs are designed to be rolled up such that the anterior surface of the IOL is on the inside of the rolled up IOL and the haptics are inside the rolled up optic or anterior to the optic. In this case, the IOL optic enters into the lens capsule first and the haptics enter last (in this situation the inserter would have a reverse orientation with the rolling member on the upper part of the insertion channel.). The IOL rolling member allows this proper rolling of the IOL such that the desired orientation and configuration is achieved.

FIGS. 12-24 illustrate aspects of pusher 12 and introducer sheath 26 (an IOL is not depicted for purposes of clarity).

Figure 13:
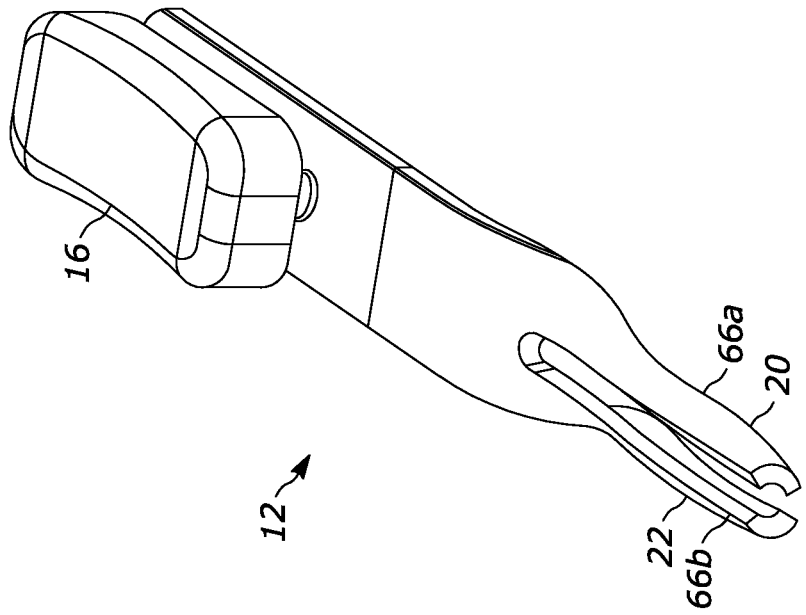
FIG. 13 is a perspective view of the pusher of FIG. 12 depicting the configuration of the distal prongs in a deformed state.
Figure 12:
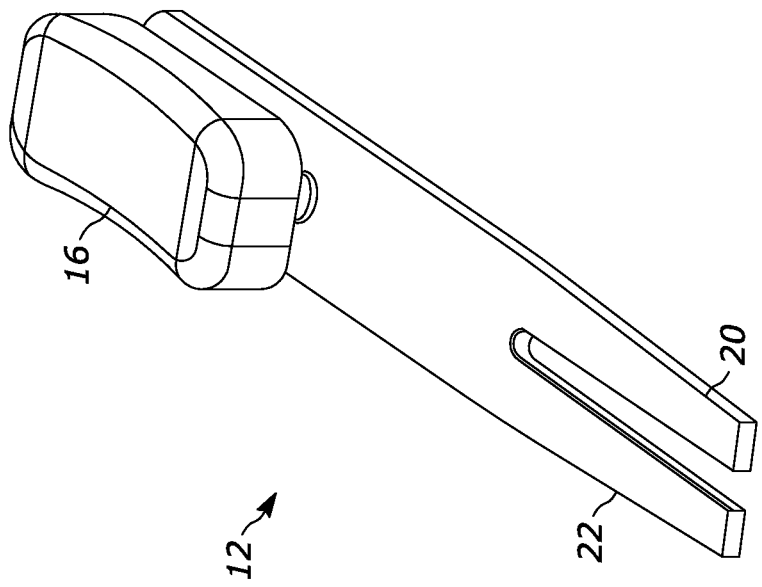
FIG. 12 is a perspective view of the pusher of FIG. 1.
Figure 14:
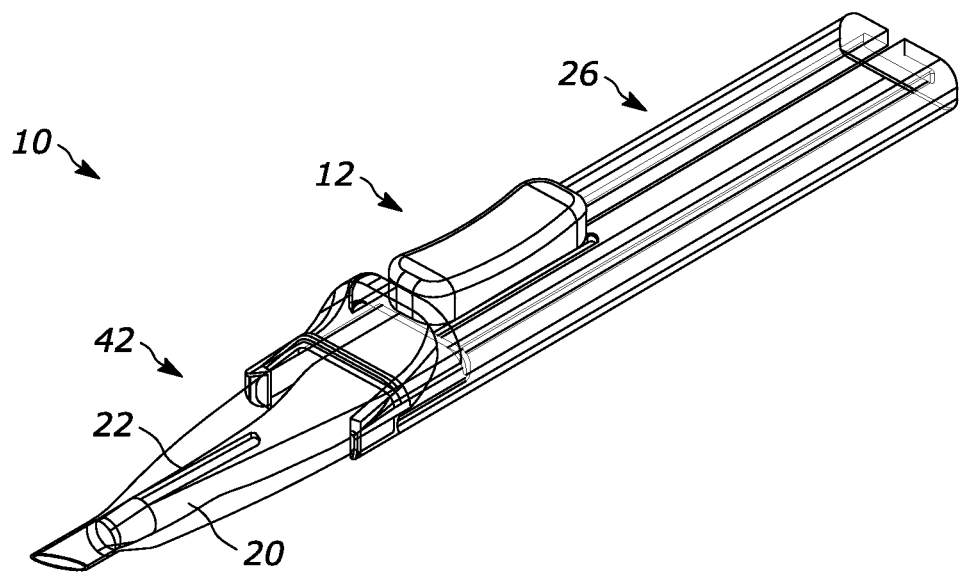
FIG. 14 is a perspective view of the insertion system with the pusher of FIG. 13 with the distal prongs positioned in the front housing of the introducer sheath.
Figure 15:
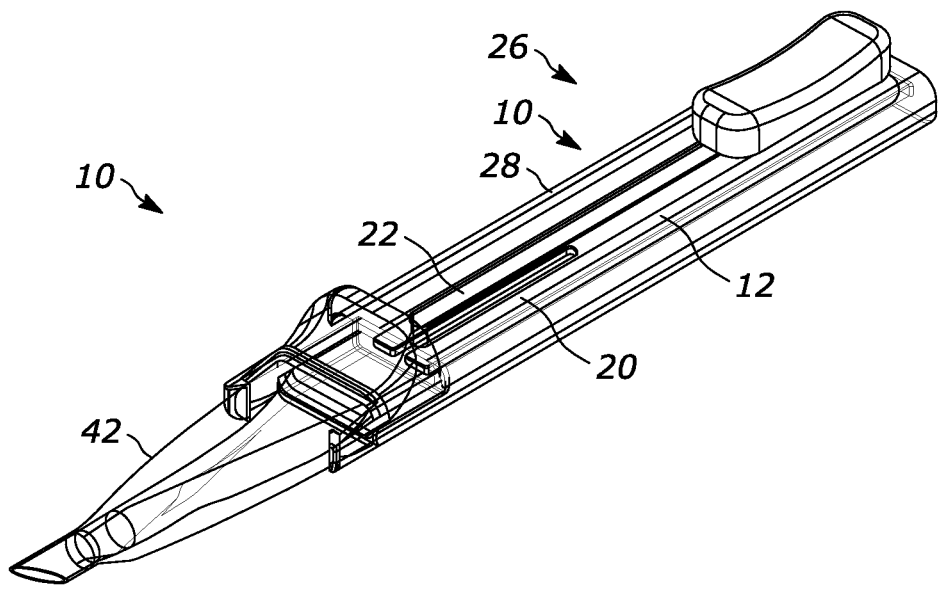
FIG. 15 is a perspective view of the insertion system with the pusher depicted in FIG. 12 positioned in the back housing of the introducer sheath.
Figure 16:
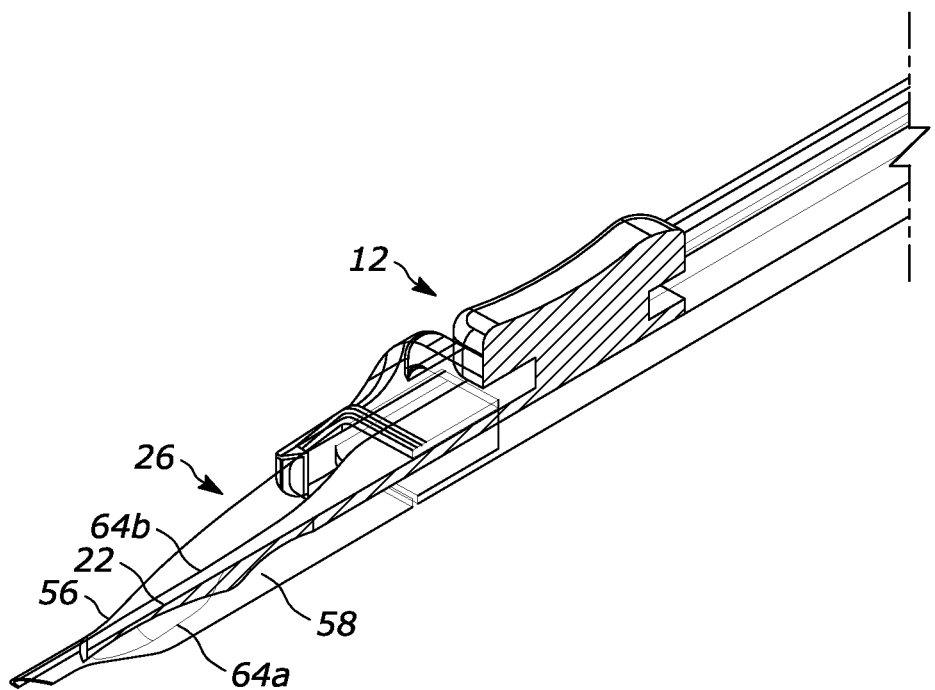
FIG. 16 is cross-sectional view of the insertion system of FIG. 1 in an assembled configuration.
Figure 17:
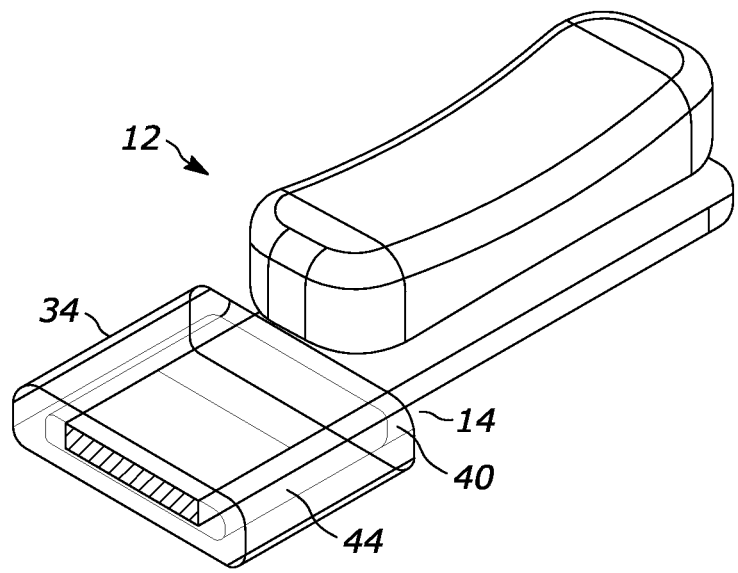
FIGS. 17-23 are cut-away views of sections of the pusher, the front housing, and the chamber of the back housing of the insertion system of FIG. 1.
Figure 18:
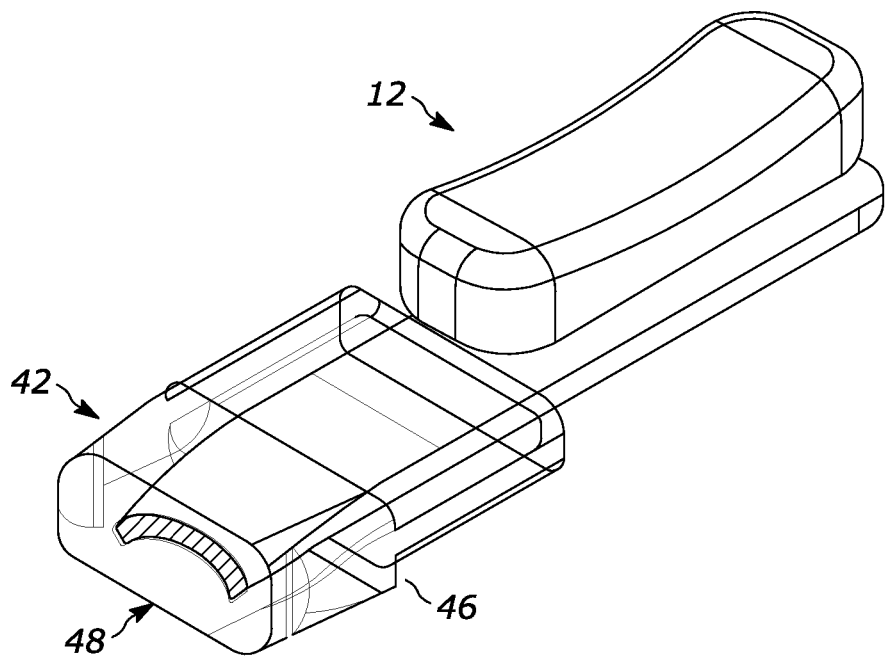
Figure 19:
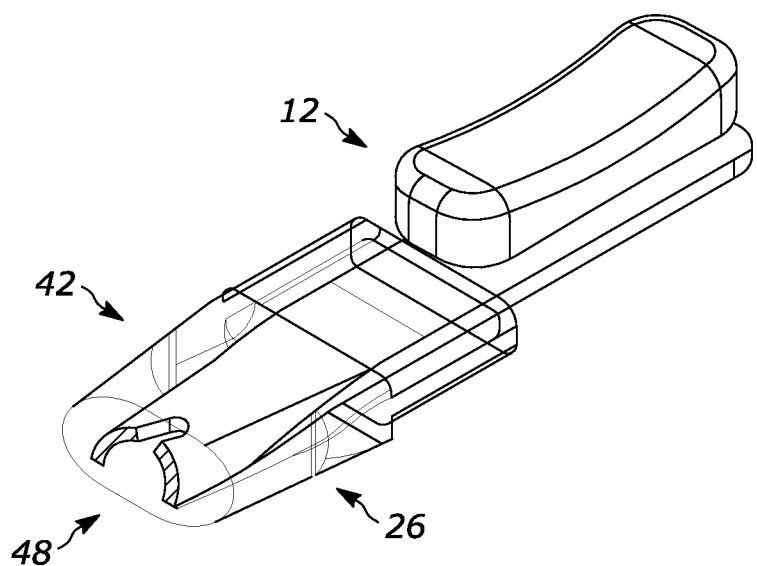
Figure 20:
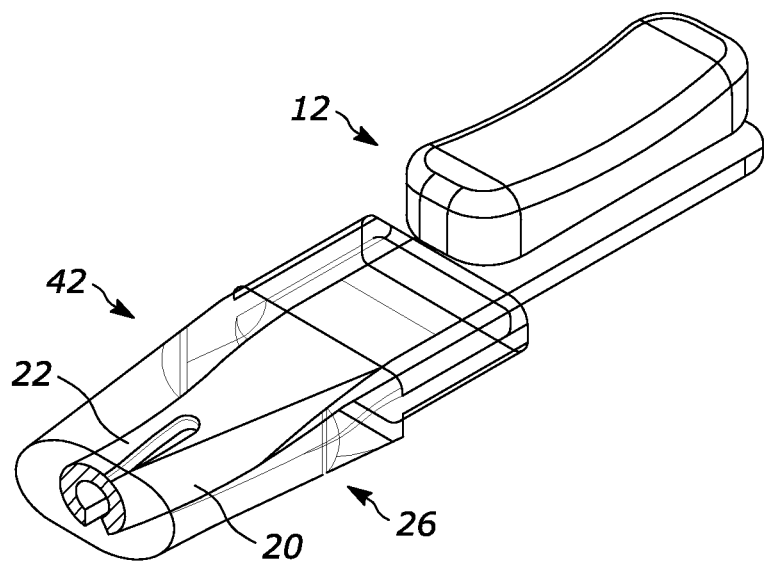
Figure 21:
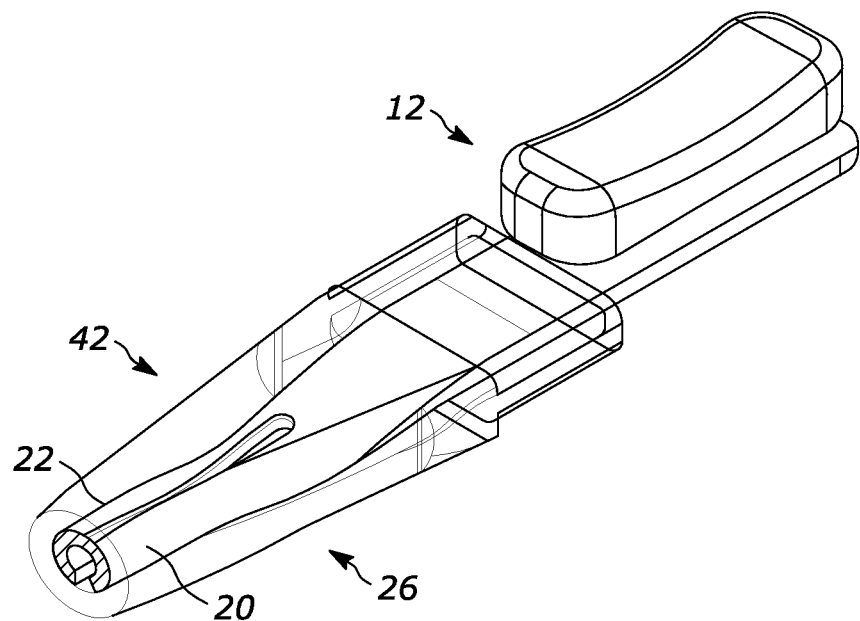
Figure 22:
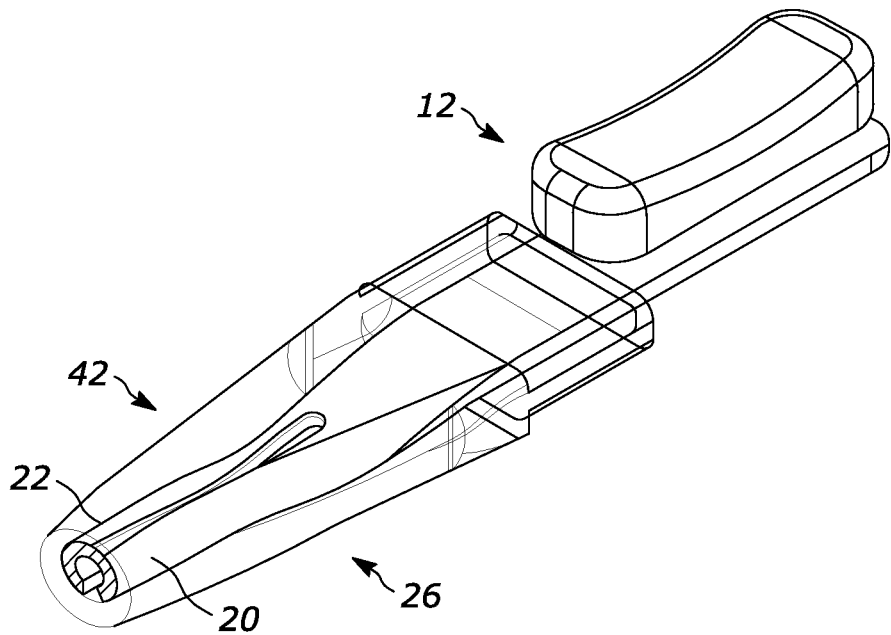
Figure 23:
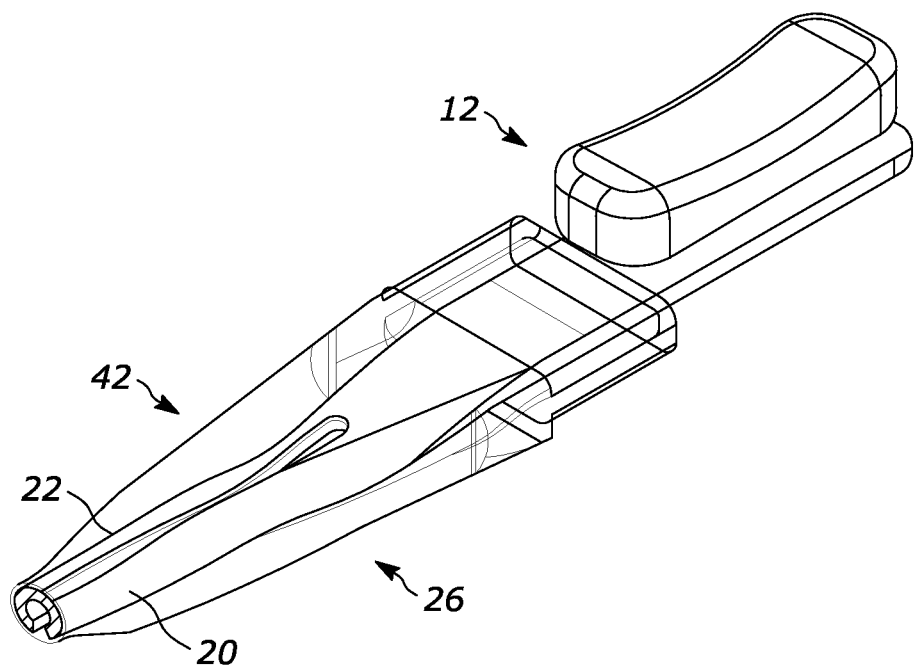
Figure 24:
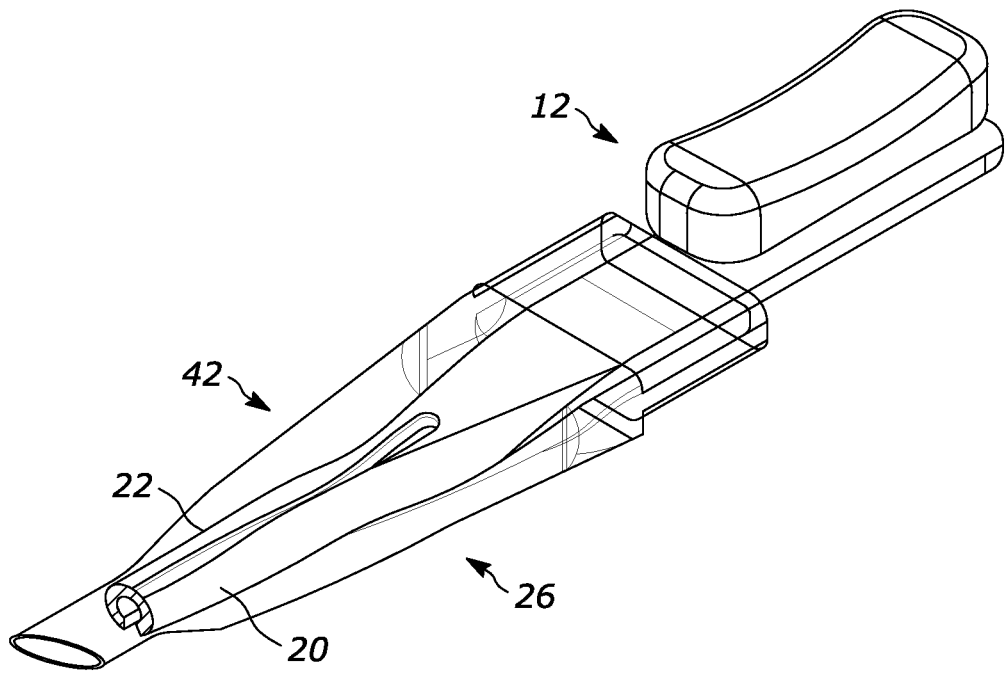
FIG. 24 is a perspective view of the pusher, the front housing, the chamber of the back housing, and the distal end of the introducer sheath of FIG. 1.

FIG. 12 illustrates the configuration of pusher 12 prior to insertion into the introducer sheath or when confined to back housing 28 of introducer sheath as depicted in FIG. 15. Prongs 22 and 20 are substantially straight. FIG. 13 illustrates the configuration of pusher 12 when inserted into the introducer sheath (not shown for purposes of clarity) and when the prongs have entered front housing 42. Because the prongs can be deformable, the prongs can assume a curved configuration. In particular and with reference to FIGS. 14 and 16, the IOL rolling member 48 can have a first inner side wall 64a and a second inner side wall 64b each having a curved concave configuration. The outer surface 66a and 66b of the respective first and second prongs 20 and 22 can be deformable to have a curved configuration complementary to the curved configuration of the respective first and second inner side walls of the IOL rolling member. FIGS. 17-24 illustrate progressive partial cut-away views of the pusher 12 and the introducer sheath 26. FIG. 17 illustrates proximal portion 14 of pusher 12 against abutment face 40 and the section of the pusher distal to actuator 16 disposed in receptacle 44, which in turn, is disposed in chamber 34. FIG. 18 is a partial cut-away view of pusher 12 illustrating the initial interaction between pusher 12 and IOL rolling member 48. FIG. 19-24 are further progressive partial cut-away views of the pusher 12 as it is being urged through introducer sheath 26. The figures depict the curvature of prongs 20 and 22, which as stated above, have a curved configuration complimentary to the curved configuration of the respective first and second inner walls of the IOL rolling member.

Figure 25:
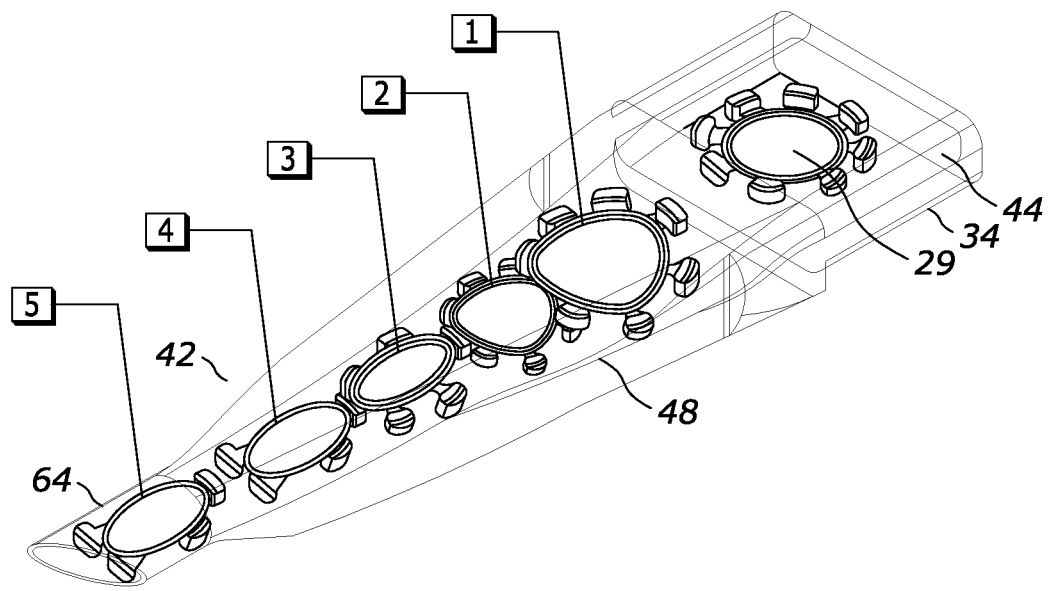
FIG. 25 is a perspective view of the front housing, distal end, and chamber of the back housing of the introducer sheath of FIG. 1 schematically illustrating an IOL at different locations in the front housing as the IOL passes through the front housing and interacts with the IOL rolling member.
Figure 32:
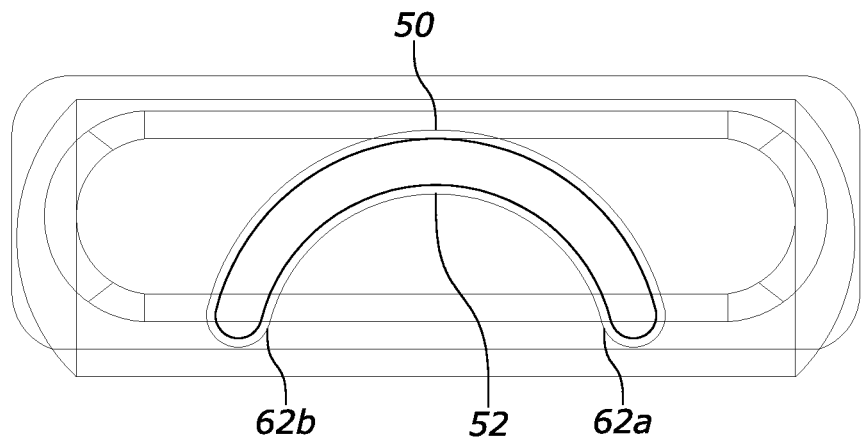
FIG. 32 is a cross-sectional view along lines II-II in FIG. 30.
Figure 33:
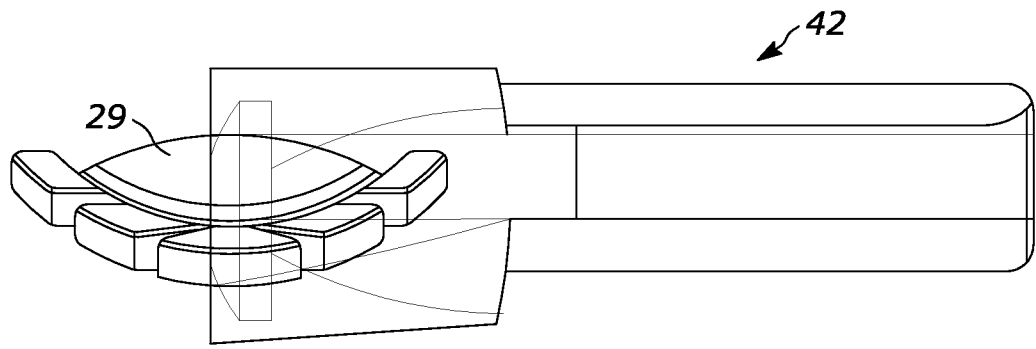
FIG. 33 is side view of the portions of the introducer sheath and the IOL depicted in FIG. 31.
Figure 34:
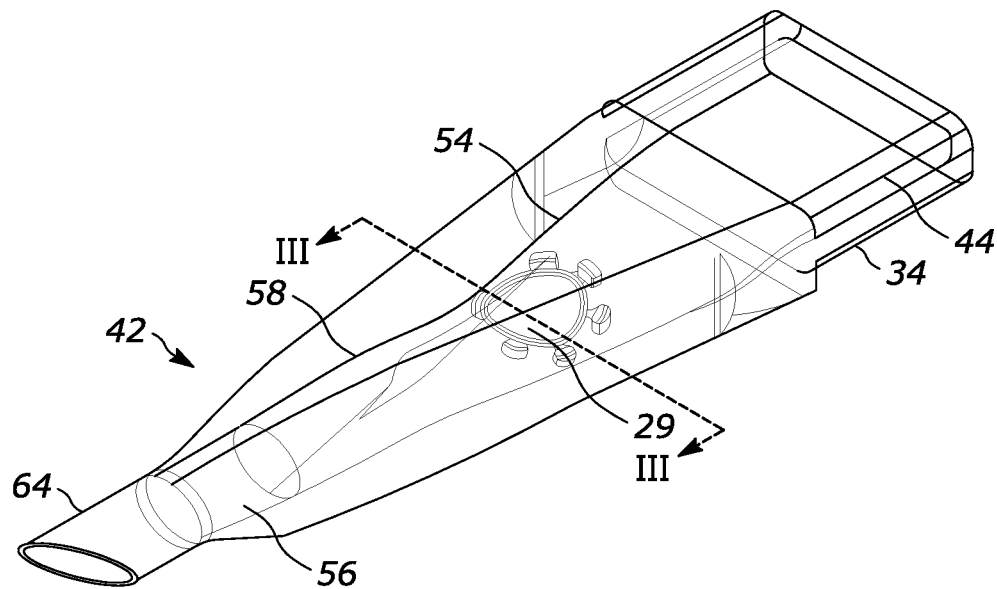
FIG. 34 is a perspective view of the front housing, distal end, and the chamber of the back housing of the introducer sheath of FIG. 25 schematically illustrating the IOL interacting with the IOL rolling member between the proximal section and intermediate section of the IOL rolling member.

FIG. 25 schematically illustrates IOL 29 at different locations in front housing 42 and the configuration of the IOL at these different locations as the IOL passes through the front housing and interacts with the IOL rolling member. The pusher of the insertion system is not shown for purposes of clarity. Location (1) illustrates the initial bending of IOL 29 at the entry of the longitudinally extending lumen of rolling member 48. Location (2) illustrates the rolling of IOL 29 which is generally controlled by the top surface of IOL rolling member 48. Location (3) illustrates full rolling of IOL 29 that is ensured by the intermediate bottom section of IOL rolling member 48. Location (4) illustrates fully rolled IOL 29 undergoing radial compression. Location (5) illustrates fully rolled IOL 29 at maximum compression into distal end 64. FIGS. 26-29 illustrate different views of IOL 29 in front housing 42 when IOL 29 interacts with rolling member 48 at location (1); FIGS. 30-33 are different views of IOL 29 in front housing 42 when IOL 29 interacts with rolling member 48 at location (2); FIGS. 34-27 are different views of IOL 29 in front housing 42 when IOL 29 interacts with rolling member 48 at location (3); FIGS. 38-41 are different views of IOL 29 in front housing 42 when IOL 29 interacts with rolling member 48 at location (4); FIGS. 42-45 are different views of IOL 29 in front housing 42 when IOL 29 interacts with rolling member 48 at a location between location (4) and location (5); FIGS. 46-49 are different views of IOL 29 in front housing 42 when IOL 29 interacts with rolling member 48 at location (5).

Figure 26:
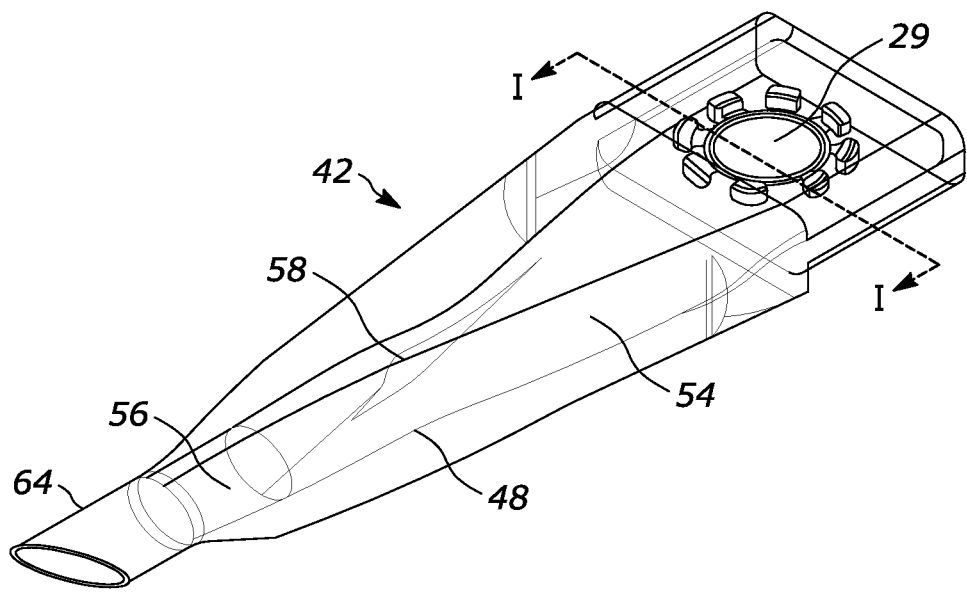
FIG. 26 is a perspective view of the front housing, distal end, and chamber of the back housing of the introducer sheath of FIG. 25 schematically illustrating the IOL in the receptacle of the front housing and the receptacle disposed in the chamber of the back housing.
Figure 27:
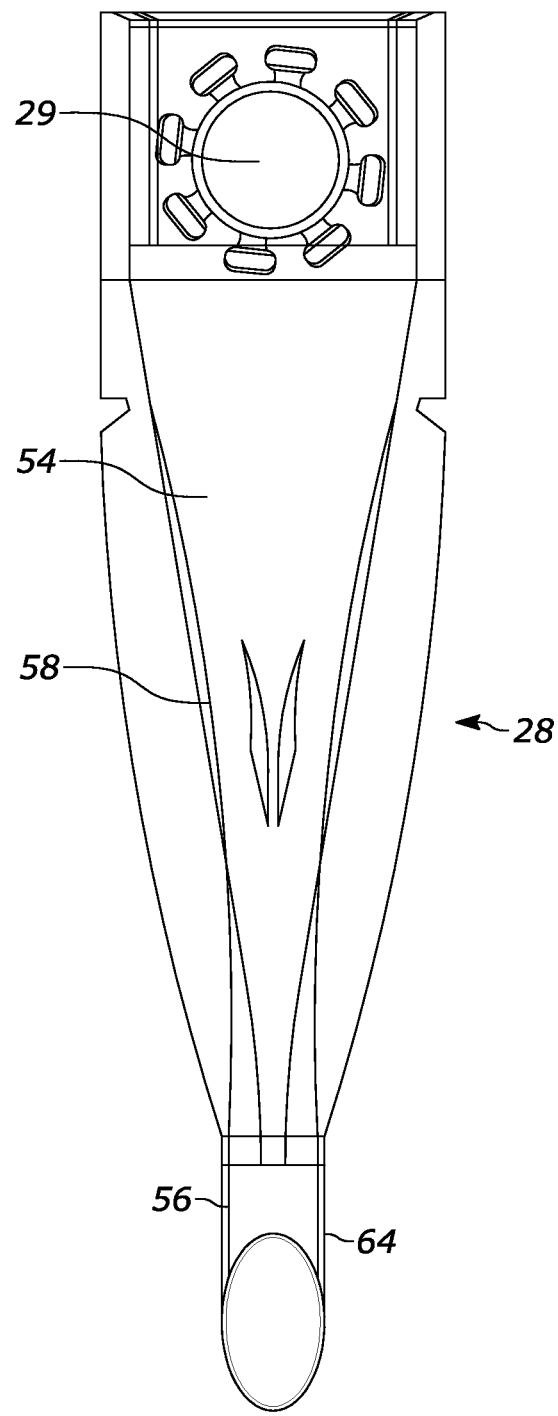
FIG. 27 is a top view of the portions of the introducer sheath and the IOL depicted in FIG. 26.
Figure 28:
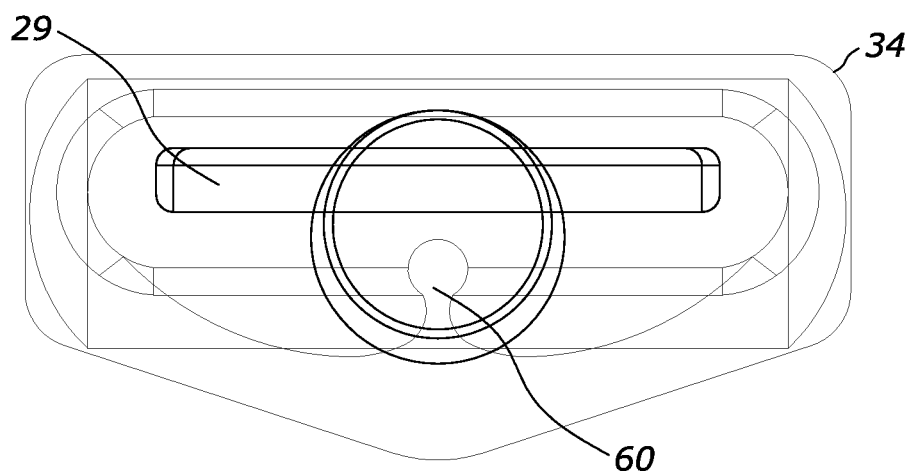
FIG. 28 is a cross-sectional view along lines I-I in FIG. 26.
Figure 29:
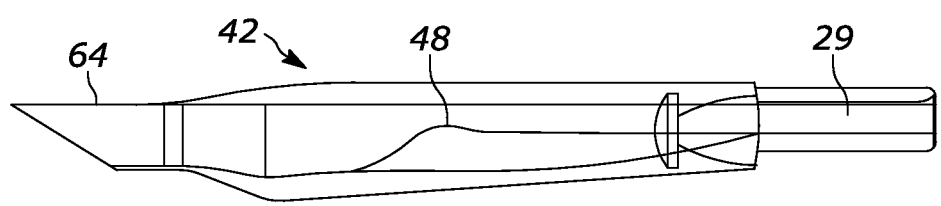
FIG. 29 is side view of the portions of the introducer sheath and the IOL depicted in FIG. 27.

In particular, FIG. 26 is a perspective view of front housing 48, distal end 64, and chamber 34 of the back housing of the introducer sheath and schematically illustrating IOL 29 in receptacle 44 of front housing 48 and receptacle 44 disposed in chamber 34 of the back housing. FIG. 27 is a top view of the portions of the introducer sheath and the IOL depicted in FIG. 26. FIG. 28 is a cross-sectional view along lines I-I in FIG. 26. FIG. 29 is side view of the portions of the introducer sheath and the IOL depicted in FIG. 27.

Figure 30:
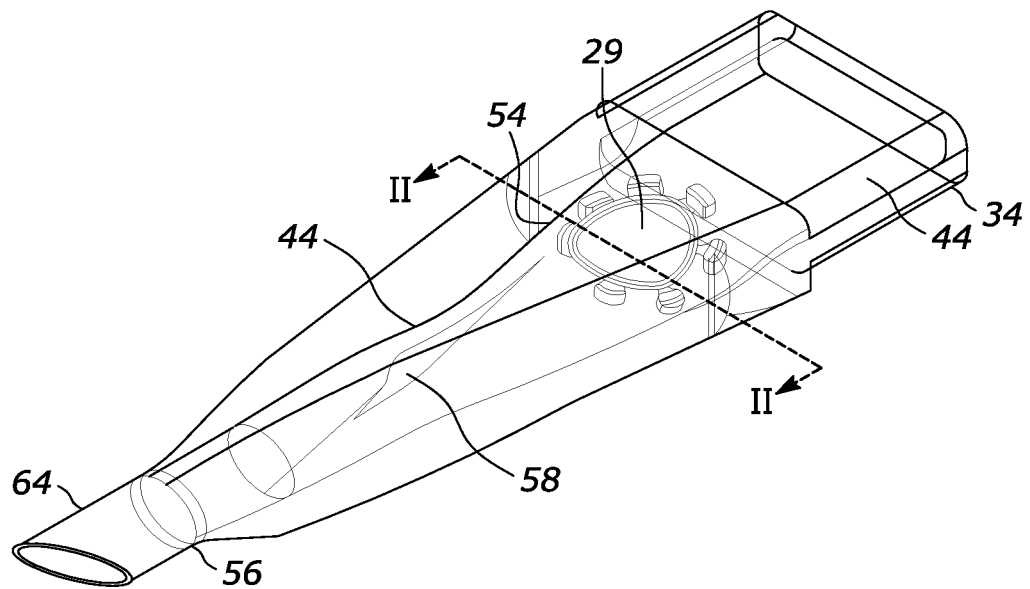
FIG. 30 is a perspective view of the front housing, distal end, and the chamber of the back housing of the introducer sheath of FIG. 25 schematically illustrating the IOL interacting with the proximal section of the IOL rolling member.
Figure 31:
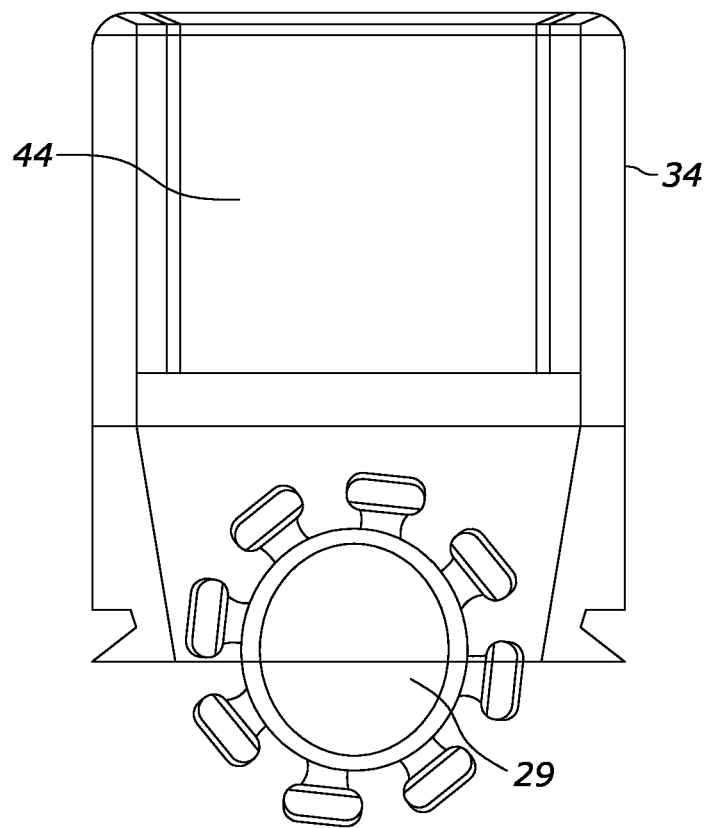
FIG. 31 is a top cut-away view of the introducer sheath and the IOL depicted in FIG. 30.

FIG. 30 is a perspective view of front housing 42, distal end 64, and chamber 34 of the back housing of the introducer sheath of FIG. 25 schematically illustrating IOL 29 interacting with proximal section 54 of IOL rolling member 48. FIG. 31 is a top cut-away view of the introducer sheath and IOL depicted in FIG. 30. FIG. 32 is a cross-sectional view along lines II-II in FIG. 30. FIG. 33 is side view of the portions of the introducer sheath and the IOL depicted in FIG. 31.

Figure 35:
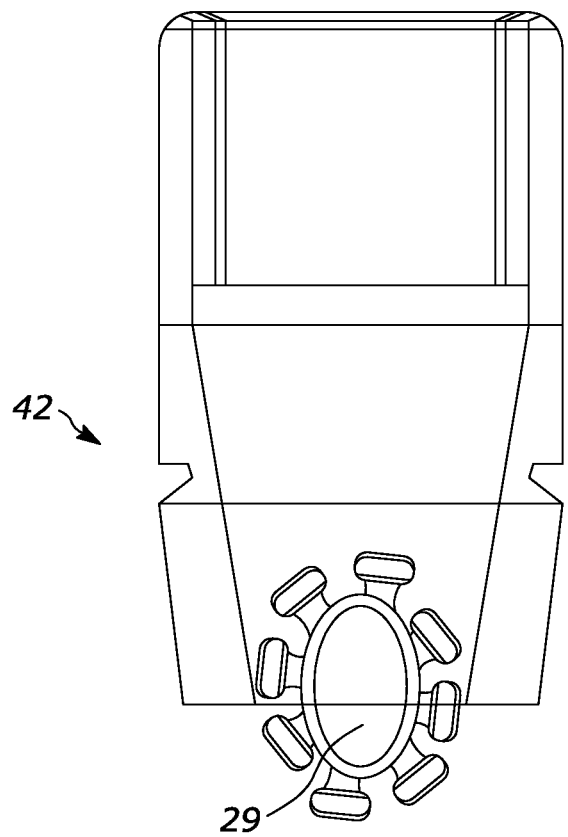
FIG. 35 is a top cut-away view of the introducer sheath and the IOL depicted in FIG. 34.
Figure 36:
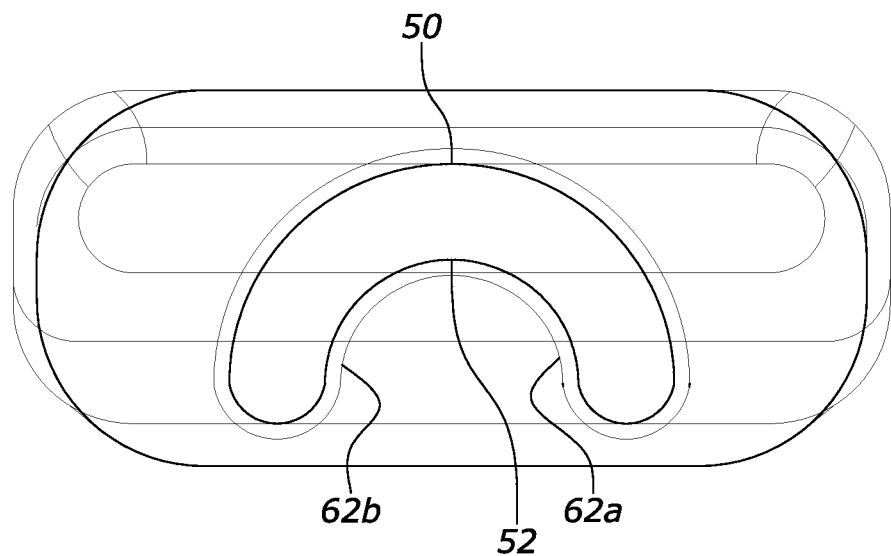
FIG. 36 is a cross-sectional view along lines III-III in FIG. 34.
Figure 37:
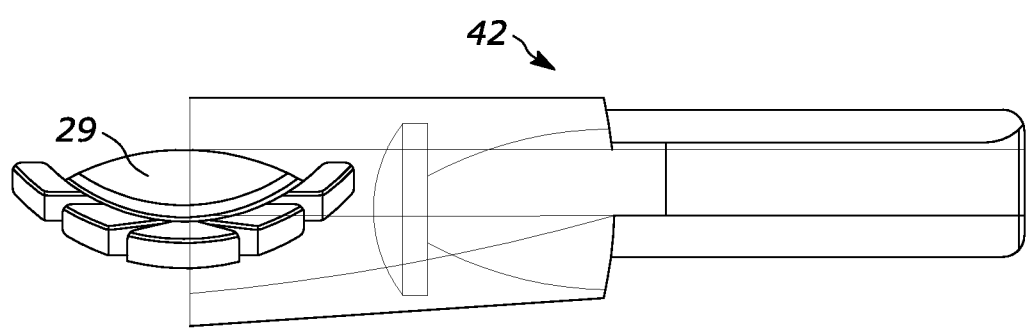
FIG. 37 is side view of the portions of the introducer sheath and the IOL depicted in FIG. 35.

FIG. 34 is a perspective view of front housing 42, distal end 64, and chamber 34 of the back housing of the introducer sheath of FIG. 25 schematically illustrating IOL 29 interacting with IOL rolling member 48 between proximal section 54 and intermediate section 58 of IOL rolling member 48. FIG. 35 is a top cut-away view of the introducer sheath and the IOL depicted in FIG. 34. FIG. 36 is a cross-sectional view along lines III-III in FIG. 34. A comparison of FIG. 32 and FIG. 36 illustrates the radius of curvature of faces 50 and 52 defining the longitudinally extending lumen 60 of IOL rolling member 48 decreasing as the IOL is positioned further distal in front housing 42 and the distance between opposing inner peripheral edges 62a and 62 of lower face 52 decreasing. FIG. 37 is side view of the portions of the introducer sheath and IOL depicted in FIG. 35.

Figure 38:
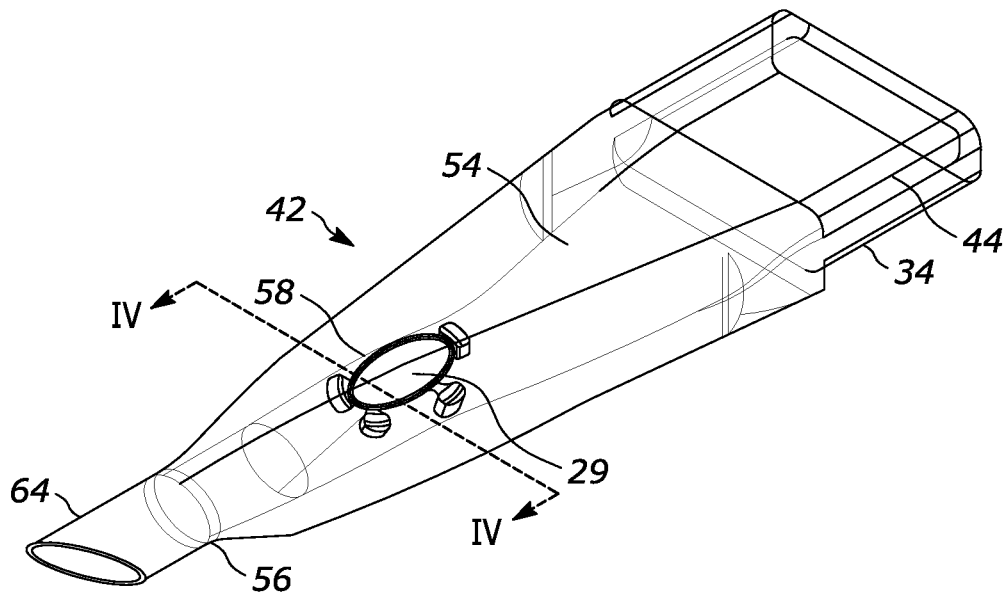
FIG. 38 is a perspective view of the front housing, distal end, and the chamber of the back housing of the introducer sheath of FIG. 25 schematically illustrating the IOL interacting with the intermediate section of the IOL rolling member.
Figure 39:
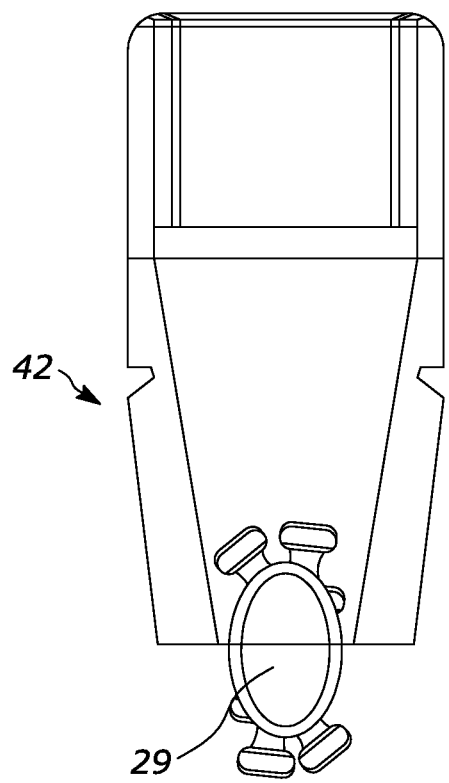
FIG. 39 is a top cut-away view of the introducer sheath and the IOL depicted in FIG. 38.
Figure 40:
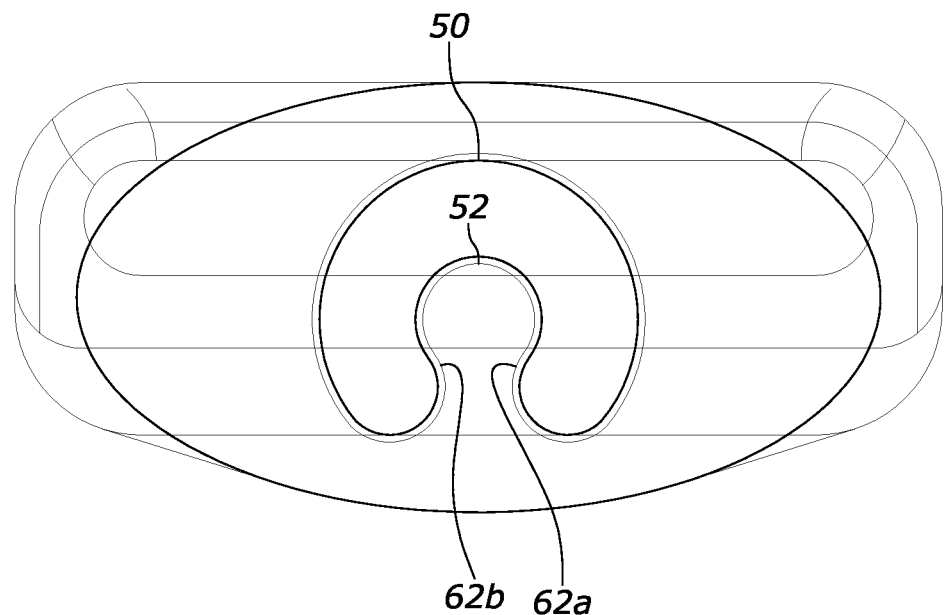
FIG. 40 is a cross-sectional view along lines IV-IV in FIG. 38.
Figure 41:
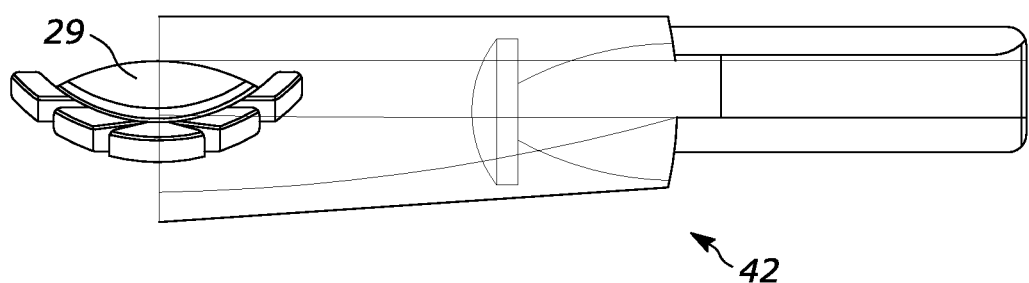
FIG. 41 is side view of the portions of the introducer sheath and the IOL depicted in FIG. 39.

FIG. 38 is a perspective view of front housing 42, distal end 64, and chamber 34 of the back housing of the introducer sheath of FIG. 25 schematically illustrating IOL 29 interacting with intermediate section 58 of IOL rolling member 48. FIG. 39 is a top cut-away view of the introducer sheath and IOL depicted in FIG. 38. FIG. 40 is a cross-sectional view along lines IV-IV in FIG. 38. A comparison of FIG. 40 and FIG. 36 illustrates the radius of curvature of faces 50 and 52 defining the longitudinally extending lumen 60 of IOL rolling member 48 decreasing as the IOL is positioned further distal in front housing 42 and the distance between opposing inner peripheral edges 62a and 62 of lower face 52 decreasing. FIG. 41 is side view of the portions of the introducer sheath and the IOL depicted in FIG. 39.

Figure 42:
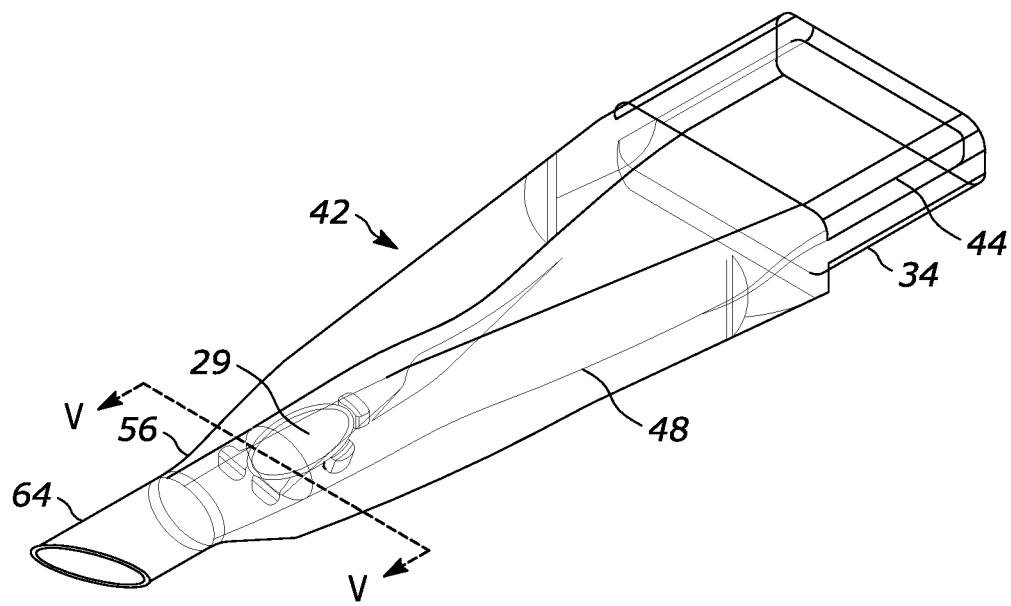
FIG. 42 is a perspective view of the front housing, distal end, and the chamber of the back housing of the introducer sheath of FIG. 25 schematically illustrating the IOL interacting with the intermediate section and part of the distal section of the IOL rolling member.
Figure 43:
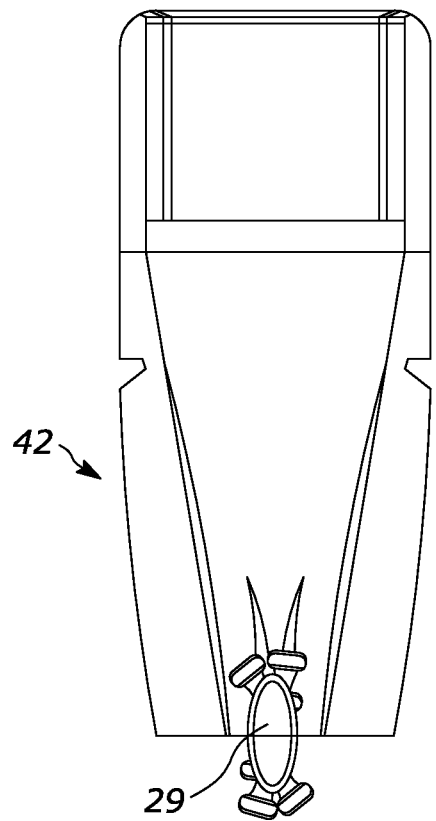
FIG. 43 is a top cut-away view of the introducer sheath and the IOL depicted in FIG. 42.
Figure 44:
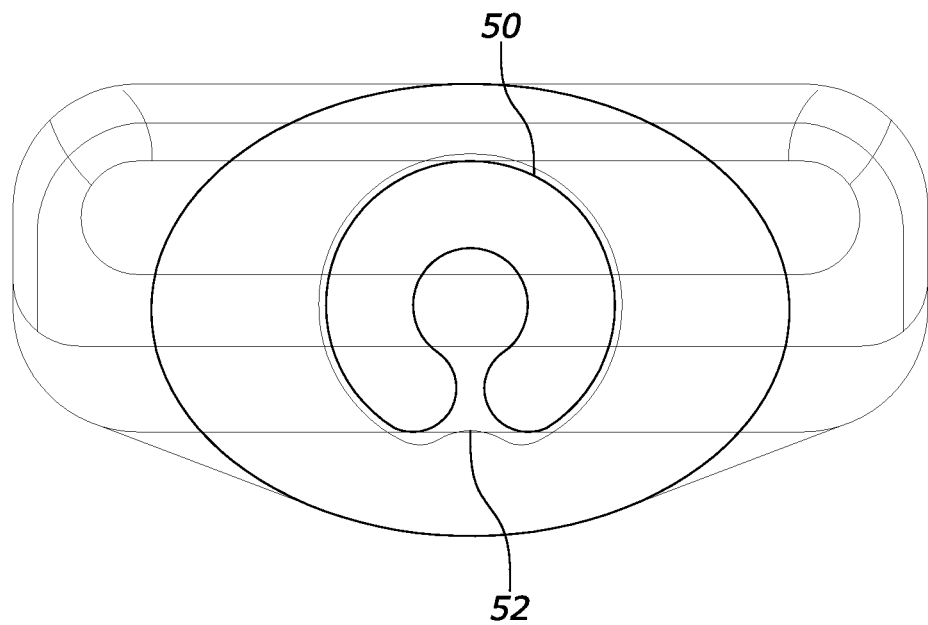
FIG. 44 is a cross-sectional view along lines V-V in FIG. 42.

FIG. 42 is a perspective view of front housing 42, distal end 64, and chamber 34 of the back housing of the introducer sheath of FIG. 25 schematically illustrating IOL 29 interacting with intermediate section 58 and part of distal section 56 of IOL rolling member 48. FIG. 43 is a top cut-away view of the introducer sheath and the IOL depicted in FIG. 42. FIG. 44 is a cross-sectional view along lines V-V in FIG. 42. A comparison of FIG. 40 and FIG. 44 illustrates the radius of curvature of faces 50 and 52 defining the longitudinally extending lumen 60 of IOL rolling member 48 decreasing as the IOL is positioned further distal in front housing 42 and the distance between opposing inner peripheral edges 62a and 62 of lower face 52 decreasing.

Figure 45:
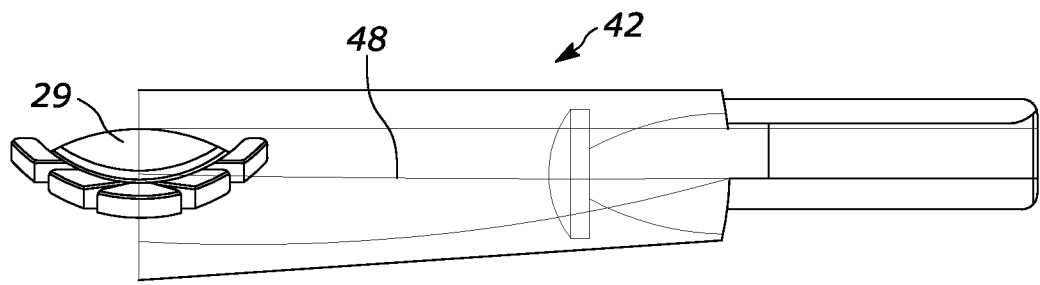
FIG. 45 is side view of the portions of the introducer sheath and the IOL depicted in FIG. 43.

FIG. 45 is side view of the portions of the introducer sheath and the IOL depicted in FIG. 43.

Figure 46:
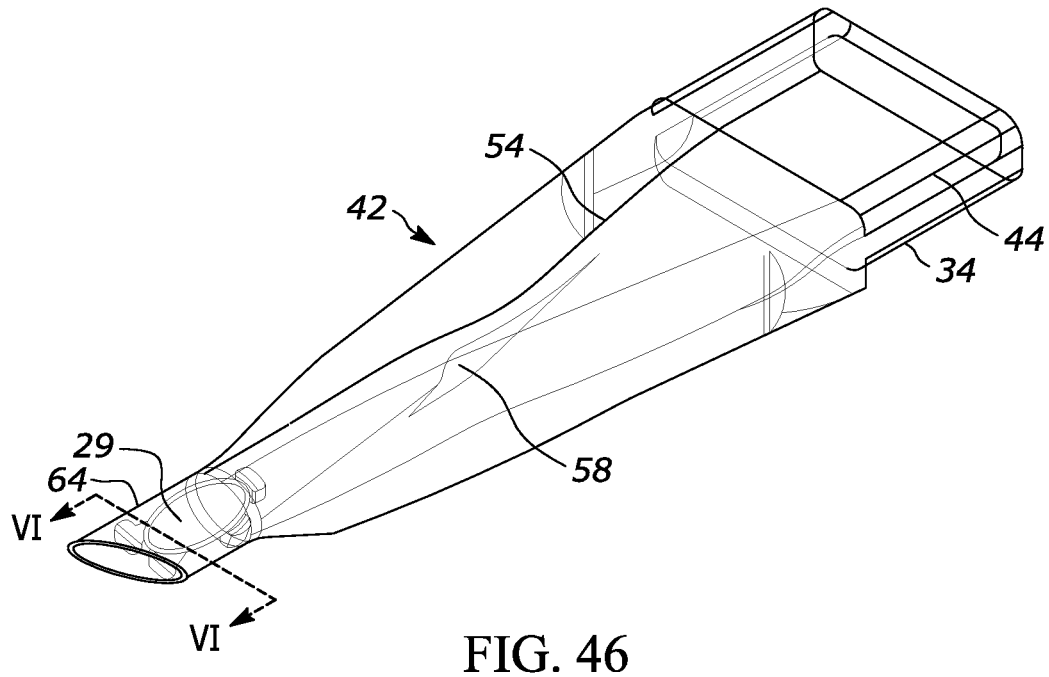
FIG. 46 is a perspective view of the front housing, distal end, and the chamber of the back housing of the introducer sheath of FIG. 25 schematically illustrating the IOL interacting with the distal section of the IOL rolling member.
Figure 47:
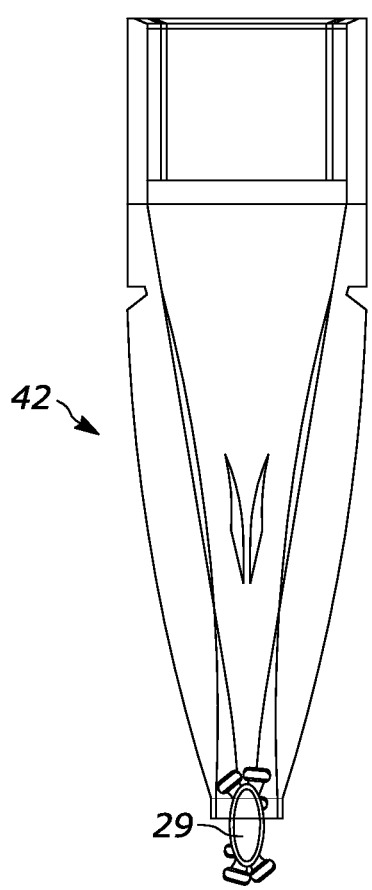
FIG. 47 is a top cut-away view of the introducer sheath and the IOL depicted in FIG. 46.
Figure 48:
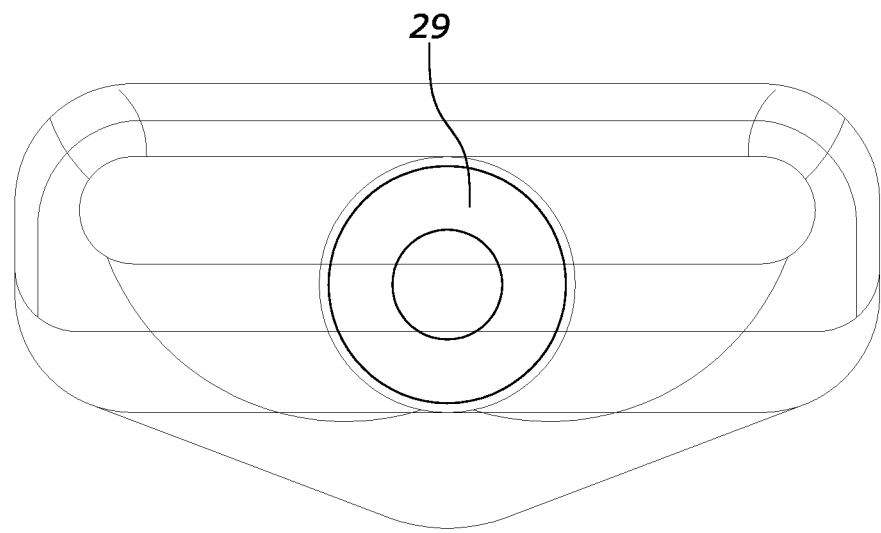
FIG. 48 is a cross-sectional view along lines VI-VI in FIG. 46.
Figure 49:
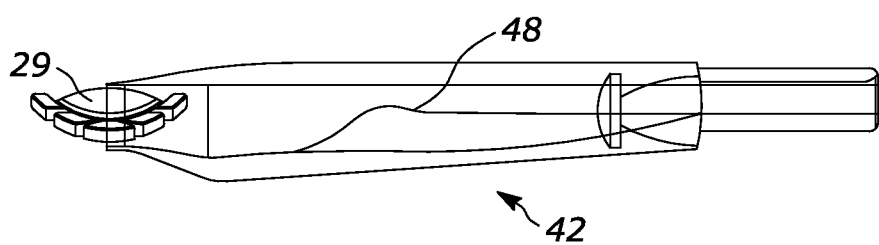
FIG. 49 is side view of the portions of the introducer sheath and the IOL depicted in FIG. 47.

FIG. 46 is a perspective view of front housing 42, distal end 64, and chamber 34 of the back housing of the introducer sheath of FIG. 25 schematically illustrating the IOL interacting with the distal section of the IOL rolling member and the distal end of the front housing. FIG. 47 is a top cut-away view of the introducer sheath and IOL depicted in FIG. 46. FIG. 48 is a cross-sectional view along lines VI-VI in FIG. 46. A comparison of FIG. 44 and FIG. 48 illustrates the radius of curvature of faces 50 and 52 defining the longitudinally extending lumen 60 of IOL rolling member 48 decreasing as the IOL is positioned further distal in front housing 42 and the distance between opposing inner peripheral edges 62a and 62 of lower face 52 decreasing such that the IOL is fully folded. FIG. 49 is side view of the portions of the introducer sheath and IOL depicted in FIG. 47.

Figure 50:
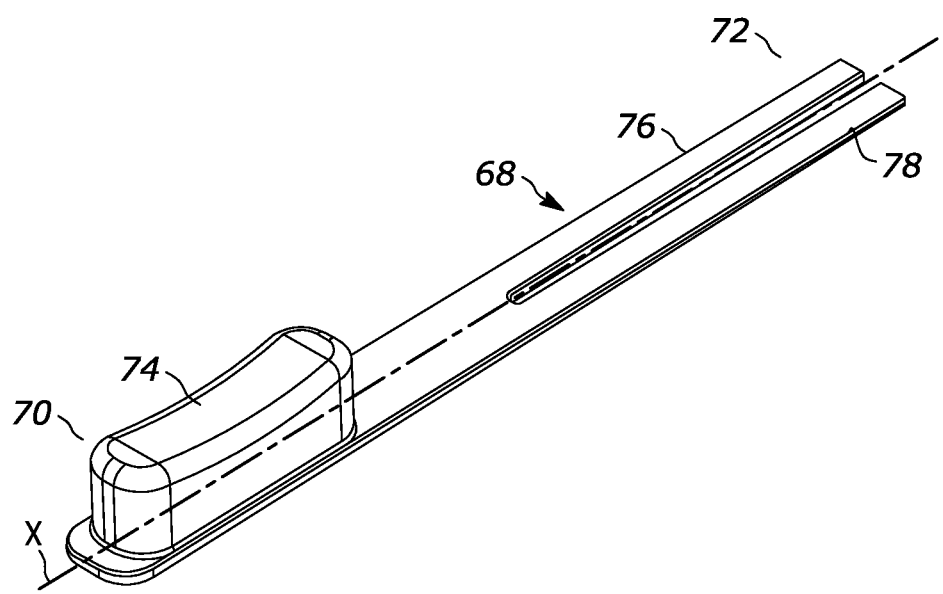
FIG. 50 is a side view of a pusher of an insertion system according to an aspect of the present disclosure.
Figure 51:
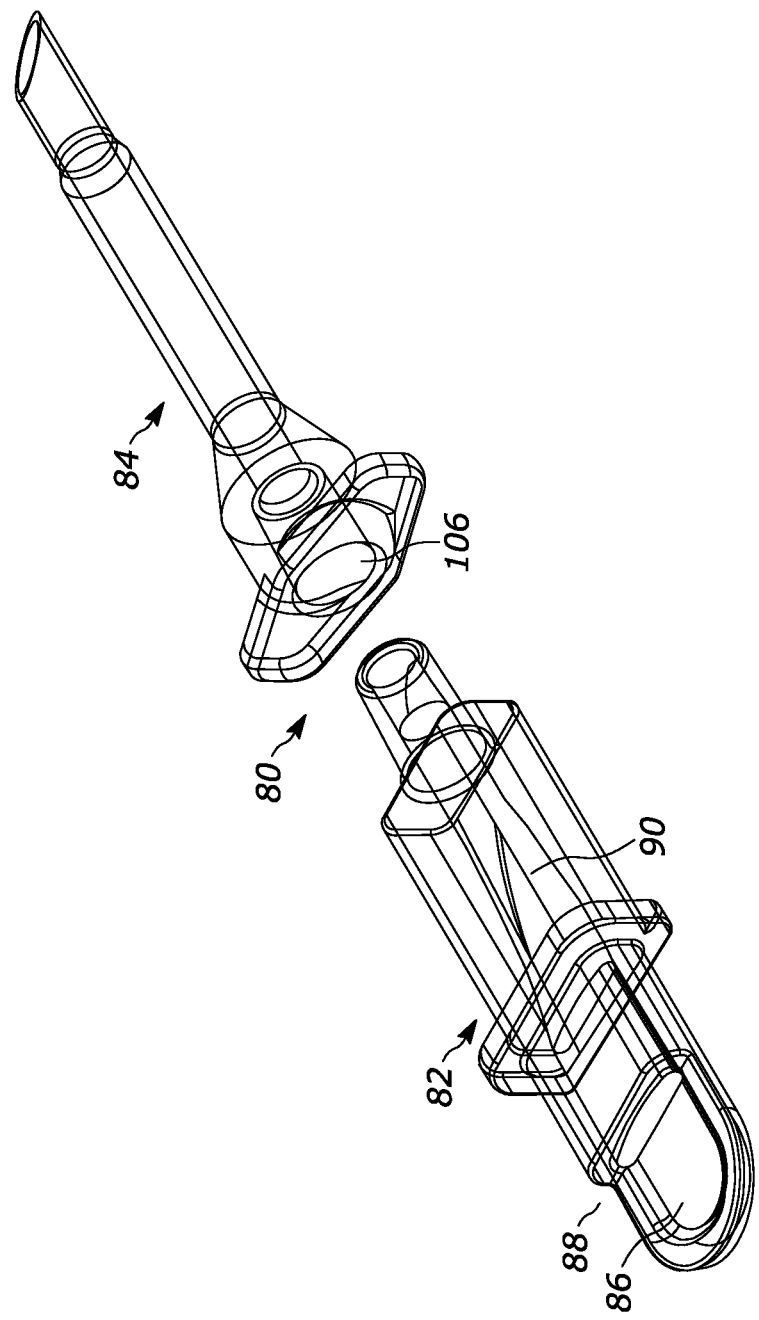
FIG. 51 is a side view of the unassembled back housing and the front housing of an introducer sheath of an insertion system according to an aspect of the present disclosure.
Figure 52:
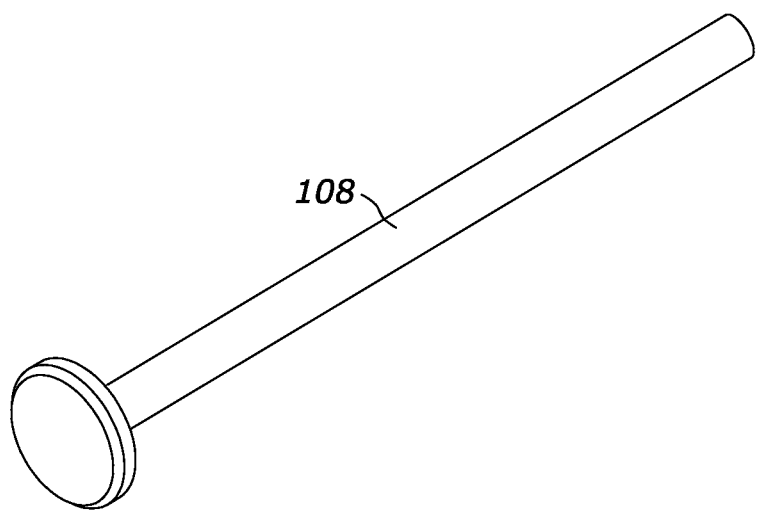
FIG. 52 is a side view of a secondary pusher of an insertion system according to an aspect of the present disclosure.
Figure 53:
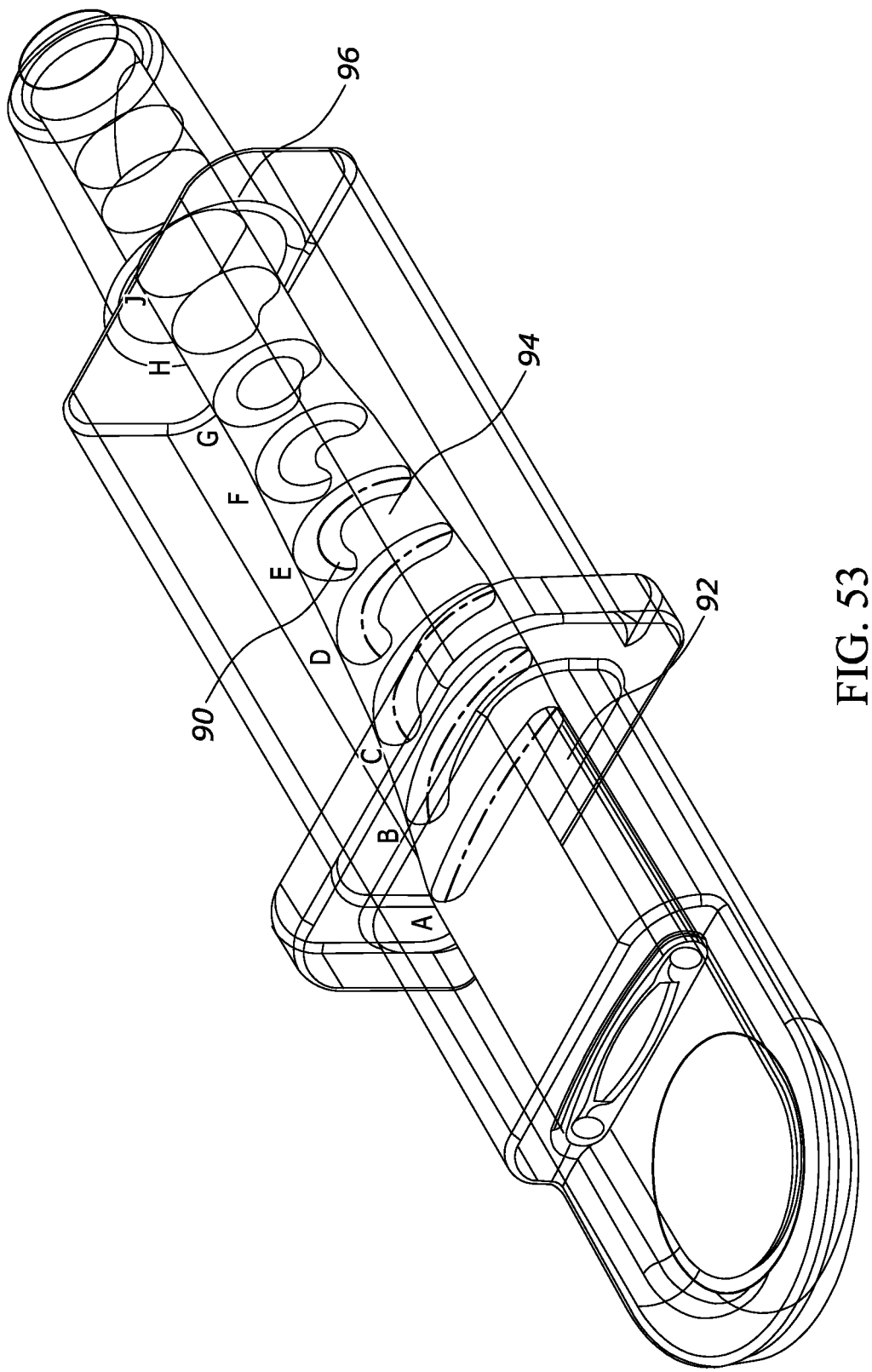
FIG. 53 is a schematic illustration of the back housing of the introducer sheath of FIG. 51 indicating several internal sections of the back housing.
Figure 54A:
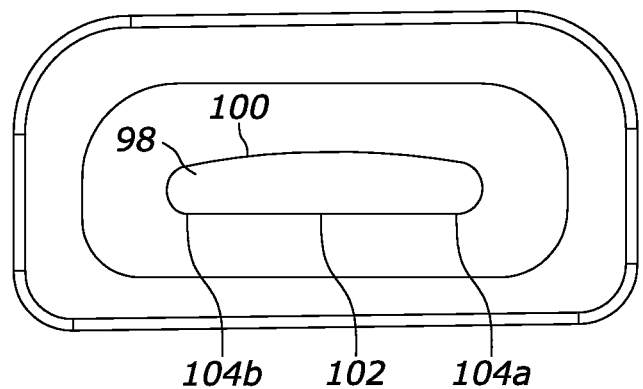
FIGS. 54A-54I are cross-sectional view of the internal sections indicated in FIG. 53.
Figure 54B:
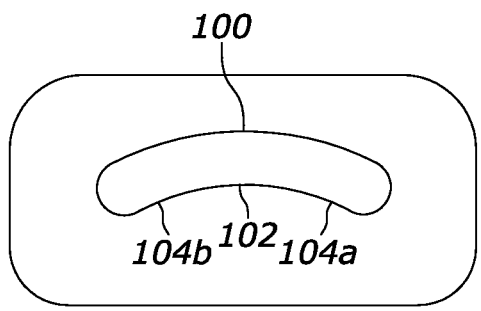
Figure 54C:
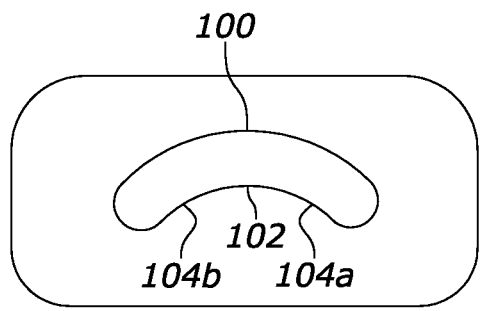
Figure 54D:
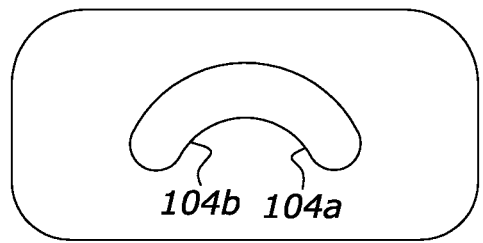
Figure 54E:
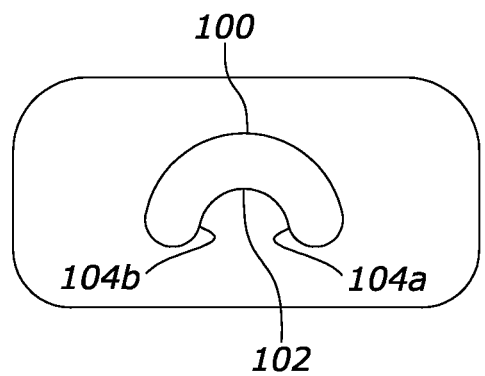
Figure 54F:
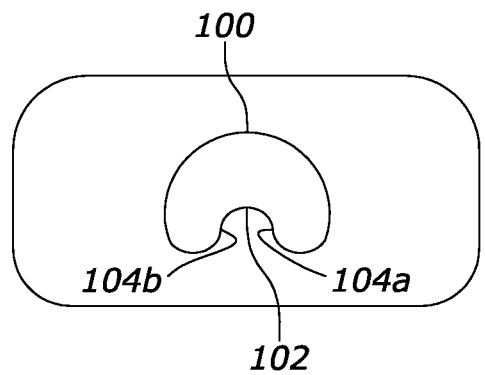
Figure 54G:
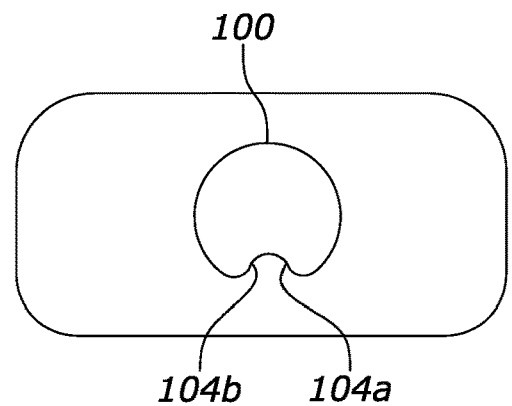
Figure 54H:
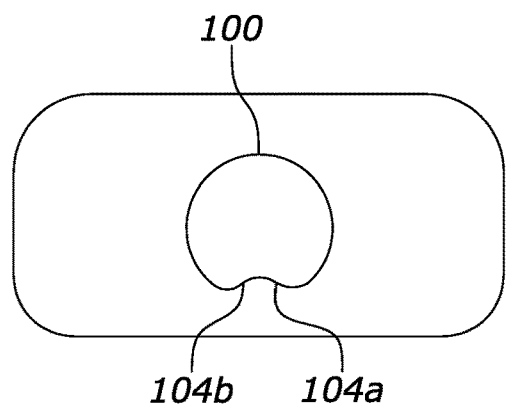
Figure 54I:
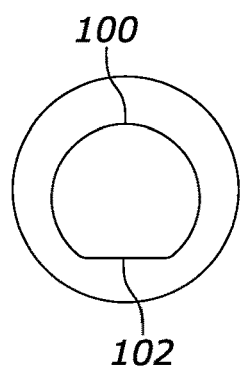

FIGS. 50-52 illustrate an insertion system according to another aspect of the present disclosure. FIG. 50 illustrates pusher 68 having a longitudinally extending axis X and comprising a proximal portion 70 and distal portion 72. Proximal portion 70 can comprise actuator 74 and distal portion 72 can comprise deformable and longitudinally extending first prong 76 and deformable and a longitudinally extending second prong 78. FIG. 51 illustrates introducer sheath 80 that can comprise back housing 82 and front housing 84. Back housing 82 can comprise receptacle 86 located at proximal portion 88 of back housing 82. Referring to FIG. 53, longitudinally extending IOL rolling member 90 can be in fluid communication with receptacle 86 and can have proximal section 92, intermediate section 94, distal section 96. Referring to FIG. 54, longitudinally extending lumen 98 can be defined by upper face 100 and lower face 102. Lower face 102 can comprise opposing inner peripheral edges 104a and 104b, wherein the radius of curvature of upper face 100 and lower face 102 decreases from proximal section 92 to distal section 94 and the distance between opposing inner peripheral edges 104a and 104b decreases from proximal section 92 to distal section 96 as depicted in FIG. 54A to 54J, which are cross-sectional views of the back housing at locations A-J identified in FIG. 53, respectively. Front housing 84 can be in fluid communication with the distal section of the IOL rolling member and can comprise longitudinally extending lumen 106. The insertion system can further comprise secondary pusher 108 displaceable in the longitudinally extending lumen of the front housing of the introducer sheath.

In use, the back housing and the front housing can be assembled together and an IOL can be placed in the receptacle of the back housing. The IOL can be urged distally over the IOL rolling member with the pusher until the IOL is in the front housing. The back housing can be removed and the secondary pusher can be used to advance the IOL through the front housing until the IOL is ultimately delivered into a patient's eye.

Figure 55:
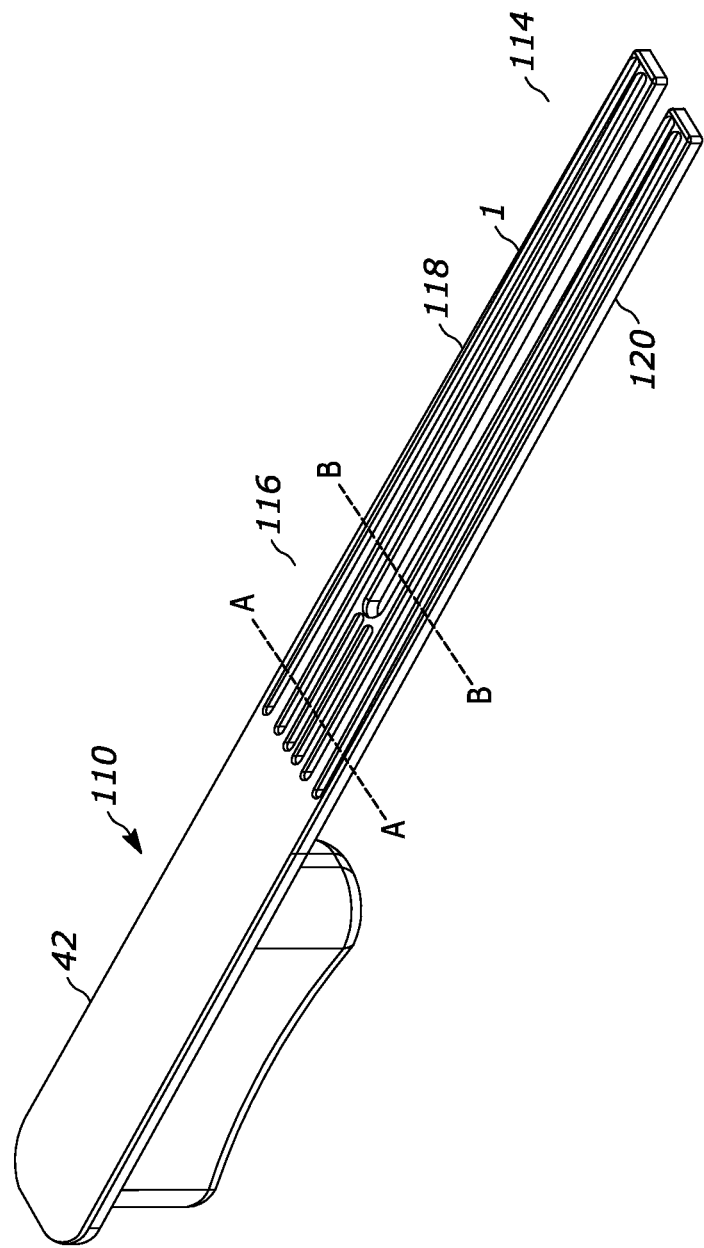
FIG. 55 is a side view of a pusher according to an aspect of the present disclosure.
Figure 56:
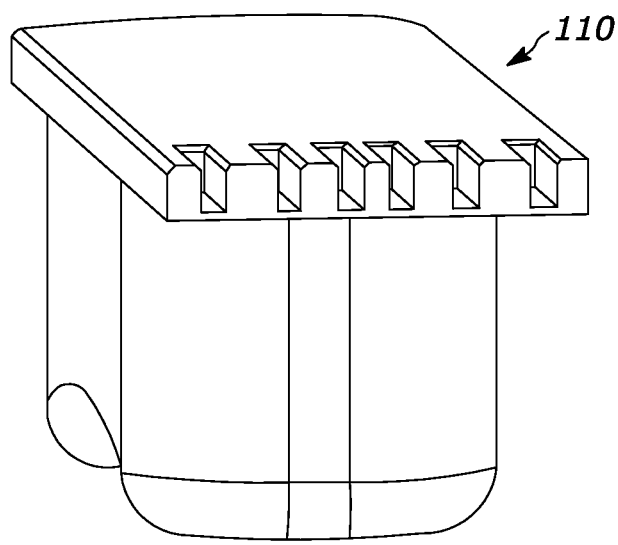
FIG. 56 is a cross sectional view of the pusher of FIG. 55 along lines A-A.
Figure 57:
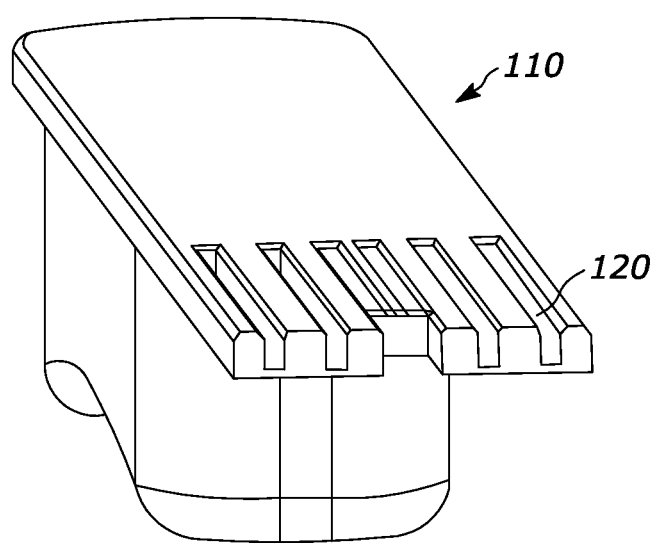
FIG. 57 is a cross-sectional view of the pusher of FIG. 55 along lines B-B.

FIGS. 55-57 depict an alternative pusher 110 that has intermediate portion 116 between proximal portion 112 and distal portion 114. Intermediate portion 116, first prong 118, and/or second prong 120 can comprise a plurality of flexures 120.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. An insertion system to insert an intraocular lens (IOL) in a patient's eye comprising:
    a pusher having a longitudinally extending axis and comprising:
        a proximal portion comprising an actuator, a distal portion comprising a deformable and longitudinally extending first prong and a deformable and longitudinally extending second prong;
    an introducer sheath comprising:
        a back housing comprising:
            a first longitudinally extending lumen sized and configured to slidably receive the first prong of the pusher; a second longitudinally extending lumen sized and configured to slidably receive the second prong of the pusher; and a chamber located at a distal portion of the back housing having a distal opening and a proximal abutment face configured to contact the pusher in a fully deployed position to limit the amount that the proximal portion of the pusher extends to or beyond a distal portion of the introducer sheath;
        a front housing comprising:
            a receptacle located at a proximal portion of the front housing that is sized and configured to receive the IOL and fit within the chamber of the back housing in an assembled configuration; and
            a longitudinally extending IOL rolling member located distal of and in fluid communication with the receptacle, the longitudinally extending 101 rolling member having a proximal section, an intermediate section, a distal section, and a longitudinally extending lumen defined by an upper face and a lower face, the lower face comprising opposing inner peripheral edges, wherein the radius of curvature of the upper face and the lower face decreases from the proximal section to the distal section and the distance between the opposing inner peripheral edges decreases from the proximal section to the distal section; and
        a distal end in fluid communication with the distal section of the IOL rolling member,
    wherein the IOL rolling member comprises a first inner side wall and an opposite second inner side wall each having a curved concave configuration,
    wherein an outer surface of each of the first and second prongs is deformable to have a curved configuration complimentary to the curved concave configuration of the respective first and second inner side walls of the IOL rolling member.

2. The insertion system of claim 1, wherein the first longitudinally extending lumen and the second longitudinally extending lumen of the back housing are located on opposing sides of the back housing.

3. The insertion system of claim 1, wherein the longitudinally extending lumen of the IOL rolling member at the proximal section and the intermediate section comprises a first side sized and configured to slidably receive the first prong of the pusher and a second side sized and configured to slidably receive the second prong of the pusher.

4. The insertion system of claim 3, wherein the first side of the longitudinally extending lumen of the IOL rolling member is configured to receive a haptic extending from a periphery of an IOL and the second side of the longitudinally extending lumen of the IOL rolling member is configured to receive an opposing haptic extending from the periphery of an IOL.

5. The insertion system of claim 3, wherein the first side of the longitudinally extending lumen of the IOL rolling member and the second side of the longitudinally extending lumen of the IOL rolling member are located on opposing sides of the IOL rolling member.

6. The insertion system of claim 3, wherein the first side of the longitudinally extending lumen of the IOL rolling member and the second side of the longitudinal extending lumen at the distal section of the IOL rolling member are in fluid communication with a single lumen defined by the distal end of the front housing.

7. The insertion system of claim 1, wherein the actuator has a surface configured to contact the proximal abutment face of the back housing in fully deployed configuration.

8. The insertion system of claim 1, wherein the pusher comprises an intermediate portion between the proximal portion and the distal portion.

9. The insertion system of claim 8, wherein the intermediate portion comprises a plurality of flexures.

10. The insertion system of claim 1, wherein the first prong and the second prong comprise a plurality of flexures.

* * * * *